(12) United States Patent
Boulanger et al.

(10) Patent No.: US 9,839,650 B2
(45) Date of Patent: *Dec. 12, 2017

(54) CHLORITE FORMULATIONS, AND METHODS OF PREPARATION AND USE THEREOF

(71) Applicant: Neuraltus Pharmaceuticals, Inc., Palo Alto, CA (US)

(72) Inventors: William Boulanger, Mahomet, IL (US); Arasteh Ari Azhir, Los Altos, CA (US)

(73) Assignee: NEURALTUS PHARMACEUTICALS, INC., San Bruno, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/996,876

(22) Filed: Jan. 15, 2016

(65) Prior Publication Data

US 2016/0129040 A1    May 12, 2016

Related U.S. Application Data

(60) Continuation of application No. 13/249,098, filed on Sep. 29, 2011, now Pat. No. 9,266,734, which is a division of application No. 11/614,859, filed on Dec. 21, 2006, now Pat. No. 8,067,035.

(60) Provisional application No. 60/753,497, filed on Dec. 22, 2005.

(51) Int. Cl.
| | | |
|---|---|---|
| A61K 33/20 | (2006.01) | |
| A61K 9/00 | (2006.01) | |
| A61K 33/00 | (2006.01) | |
| A61K 47/02 | (2006.01) | |
| C01B 11/10 | (2006.01) | |

(52) U.S. Cl.
CPC ............ *A61K 33/20* (2013.01); *A61K 9/0019* (2013.01); *A61K 33/00* (2013.01); *A61K 47/02* (2013.01); *C01B 11/10* (2013.01)

(58) Field of Classification Search
USPC ........................................................ 424/661
See application file for complete search history.

(56) References Cited

U.S. PATENT DOCUMENTS

| | | |
|---|---|---|
| 2,129,464 A | 9/1938 | Cunningham |
| 2,169,066 A | 8/1939 | Cunningham |
| 3,082,146 A | 3/1963 | Wentworth et al. |
| 4,296,103 A | 10/1981 | Laso |
| 4,507,285 A | 3/1985 | Kuhne |
| 4,725,437 A | 2/1988 | Kuhne |
| 4,851,222 A | 7/1989 | Kuhne et al. |
| 4,944,920 A | 7/1990 | Rubinstein |
| 5,078,908 A | 1/1992 | Ripley et al. |
| 5,489,435 A | 2/1996 | Ratcliff |
| 5,503,847 A | 4/1996 | Queen et al. |
| 5,622,725 A | 4/1997 | Kross |
| 5,639,295 A | 6/1997 | Wellinghoff et al. |
| 5,723,095 A | 3/1998 | Fricker et al. |
| 5,782,992 A | 7/1998 | Frangione |
| 5,830,511 A | 11/1998 | Mullerate et al. |
| 5,855,922 A | 1/1999 | Danner et al. |
| 5,877,222 A | 3/1999 | McGrath |
| 6,086,922 A | 7/2000 | Kuhne |
| 6,099,855 A | 8/2000 | Mullerat et al. |
| 6,132,702 A | 10/2000 | Witt et al. |
| 6,350,438 B1 | 2/2002 | Witt et al. |
| 6,488,965 B1 | 12/2002 | Karageozian |
| 6,703,202 B2 | 3/2004 | McGrath et al. |
| 6,706,256 B2 | 3/2004 | Lawlor |
| 8,067,035 B2 | 11/2011 | Boulanger et al. |
| 8,231,856 B2 | 7/2012 | Boulanger et al. |
| 8,501,244 B2 | 8/2013 | Boulanger et al. |
| 9,266,734 B2 | 2/2016 | Boulanger et al. |
| 2004/0037891 A1 | 2/2004 | Karagoezian |
| 2005/0181068 A1 | 8/2005 | McGrath |
| 2007/0145328 A1 | 6/2007 | Boulanger et al. |
| 2012/0015051 A1 | 1/2012 | Boulanger et al. |
| 2012/0021069 A1 | 1/2012 | Boulanger et al. |
| 2012/0021070 A1 | 1/2012 | Boulanger et al. |

FOREIGN PATENT DOCUMENTS

| | | |
|---|---|---|
| GB | 723566 A | 2/1955 |
| JP | 6230717 | 8/1994 |
| SU | 327132 | 1/1972 |
| WO | WO 99/17787 A2 | 4/1999 |
| WO | WO 99/17787 A3 | 6/1999 |
| WO | WO 03/025252 A1 | 3/2003 |
| WO | WO 03/048773 A2 | 6/2003 |
| WO | WO 03/048773 A3 | 10/2003 |

(Continued)

OTHER PUBLICATIONS

Accepta Material Safety Data Sheet. Sodium Chlorite. Jan. 6, 2004.
American Regent, "Sodium Phosphate for Injection_Product Prescribing Information" IN3405. Published online: Jul. 10, 2005.
ATSDR. Agency for Toxic Substances and Disease Registry. Public Health Statement: Chlorine Dioxide and Chlorite. Sep. 2004.
CAMEO Chemicals. Sodium chlorite. Available at http://cameochemicals.noaa.gov/chemical/1479. Accessed Jan. 12, 2009.
Cohel, et al., eds., Wound Healing, W. B. Saunders Co., Philadelphia, 1992, pp. 584-586.
Cunningham, et al. The System Sodium Chlorite-Sodium Chloride-Water at Various Temperatures. The Journal of the American Chemical Society 1955; 77(3): 799-801.
ERCO Worldwide Material Safety Data Sheet. Sodium Chlorite 5%-14%. Nov. 3, 2005.

(Continued)

*Primary Examiner* — Walter Webb
(74) *Attorney, Agent, or Firm* — Wilson Sonsini Goodrich & Rosati

(57) ABSTRACT

Described herein are chlorite formulations having a pH between about 7 and about 8.5, wherein the chlorite formulations are substantially free of deleterious non-chlorite components. Described herein are chlorite formulations, including pharmaceutical formulations, which are formulated for systemic, parenteral, or intravenous administration. Described herein are methods of preparing and methods of using the chlorite formulations described herein.

16 Claims, 2 Drawing Sheets

(56) References Cited

FOREIGN PATENT DOCUMENTS

| WO | WO 2005/076819 A2 | 8/2005 |
|---|---|---|
| WO | WO 2005/076819 A3 | 4/2006 |

OTHER PUBLICATIONS

Ercros Safety Data Sheet. Sodium Chlorite (Solution). Aug. 2009.
European search report dated Dec. 4, 2012 for EP Application No. 06847994.8.
Gordon, et al. Kinetics and mechanism of formation of chlorate ion from the hypochlorous acid/chlorite ion reaction at pH 6-10. Environ. Sci. Technol. 1991; 25:468-474.
Inorganic Ventures Certificate of Analysis—I-Cal Ion Chromatography Solution—Catalog No. ICCLO21-1; ICCLO21-5. Available at http://www.ivstandards.com/CoA/ICCLO21.pdf. Accessed Dec. 22, 2006.
Inorganic Ventures Certificate of Analysis dated Sep. 4, 2008.
Inorganic Ventures Material Safety Data Sheet—ICCLO21-1; ICCLO21-5. Dated Jul. 19, 2004. Available at http://inorganicventures.thewercselite.com/docs/ICCLO21-English,%20USA.pdf.
Inorganic Ventures. "Certificate of Analysis for 1000 µg/ml Chlorite Solution." 2008. 2 pgs.
International search report dated Oct. 29, 2007 for PCT Application No. US06/48941.
Kempf, et al. Comparative study on the effects of chlorite oxygen reaction product TCDO (tetrachlorodecaoxygen) and sodium chlorite solution (NaClO2) with equimolar chlorite content on bone marrow and peripheral blood of BDIX rats. Drugs Exp Clin Res. 1993;19(4):165-74.
Kurokawa, et al. Studies on the promoting and complete carcinogenic activities of some oxidizing chemicals in skin carcinogenesis. Cancer Lett. Oct. 1984;24(3):299-304.
LE. Pure Chlorite Developed by IV. Available at http://www.ivstandards.com/tech/articles/technical/chlorite.asp. Accessed Jan. 13, 2009.
McGrath, et al. Development of WF10, a novel macrophage-regulating agent. Curr Opin Investig Drugs. 2002; 3(3):365-73.
Moore, D. Current protocols in Molecular Biology. 1996-2000. John Willey and Sons, Inc. Appendix 2, A.2.1, A.2.7.
Nation Master. Chlorine dioxide. Available at http://www.nationmaster.com/encyclopedia/chlorine-dioxide. Accessed Jan. 12, 2009.
OxyChem Technical Data Sheet. Sodium Chlorite Health & Safety. Jan. 2009.
OxyChem Technical Data Sheet. Technical Sodium Chlorite (EPA Registered) for Chlorine Dioxide Generation. Jan. 2009.
Product Insert: Data and instruction for the Use of IMMUNOKINE WF10 (TCDO) 1.v.Solution for Intravenous Infusion. OXO Chemie. Published approximately 1997.
Qian, et al. A clean production process of sodium chlorite from sodium chlorate. Chemical Engineering Shool. South China University of Technology. Editor(s): Liu, Huanbin; Zhan, Huaiyu; Xie, Yimin. Emerging Technologies of Pulping & Papermaking, Proceedings of the International Symposium on Emerging Technologies of Pulping & Papermaking, 2nd, Guangzhou, China, Oct. 9-11, 2002: 464-471. Publisher: South China University of Technology Press, Guangzhou, China.
Science Lab.com Material Safety Data Sheet. Sodium Chlorite. Oct. 9, 2005.
Seta, et al. Acute oral toxicity and acute irritation test to skin and eye of sodium chlorite. Kagaku Keisatsu Kenkyusho Hokoku Hokagaku Hen. 1991; 44(1):7-22.
Shahangian, et al. The reaction of chloroperoxidase with chlorite and chlorine dioxide. J Biol Chem. Jun. 25, 1981;256(12):6034-40.
Sigma-Aldrich Safety Data Sheet. Sodium Chlorite. Mar. 13, 2010.
Steffen, et al. Chlorate poisoning: mechanism of toxicity. Toxicology. Nov. 12, 1993;84(1-3):217-31.
Tarimci et al. Anhydrous Sodium Chlorite. Acta Cryst. 1976; B32: 610-612.
Tissot, et al. Anti-inflammatory properties of a novel wound healing and immunomodulating agent, tetrachlorodecaoxygen complex (TCDO). Agents Actions. Nov. 1990;31(3-4):368-74.
USPC. United States Pharmacopeia and National Formulary (USP 32-NF 27). Chapters <71> Sterility Tests and <1211> Sterilization. Rockville, MD: United States Pharmacopeia Convention. Dec. 1, 2009.
USPC. United States Pharmacopeia and National Formulary (USP 32-NF 27). Chapter <1> Injections. Rockville, MD: United States Pharmacopeia Convention. Dec. 1, 2009.
Veerasarn, et al. Reduced recurrence of late hemorrhagic radiation cystitis by WF10 therapy in cervical cancer patients: a multicenter, randomized, two-arm, open-label trial. Radiother Oncol. Nov. 2004;73(2):179-85.
White, et al. Chemistry of chlorites. Industrial & Engineering Chemistry 34.7 (1942): 782-792.
U.S. Appl. No. 13/249,098 Office Action dated May 14, 2013.
U.S. Appl. No. 13/249,098 Office Action dated Jul. 27, 2015.
U.S. Appl. No. 13/249,098 Office Action dated Sep. 17, 2012.
U.S. Appl. No. 13/249,098 Office Action dated Dec. 24, 2013.
U.S. Appl. No. 13/249,098 Office Action dated Dec. 22, 2014.
U.S. Appl. No. 13/249,098 Notice of Allowance dated Dec. 17, 2015.

CHLORITE FORMULATIONS, AND METHODS OF PREPARATION AND USE THEREOF

BACKGROUND OF THE INVENTION

The chlorite ion, referred to herein as chlorite, has been used in various contexts. Sodium chlorite is a strong oxidizing agent, and has been used in water purification, disinfection, and in bleaching and deodorizing animal products. Because sodium chlorite produces highly toxic chlorine gas under acid conditions, aqueous solutions employed in commerce are usually provided as extremely basic (approximately pH 13) solutions, with the pH adjusted using sodium hydroxide.

Chlorite has also been used to treat various diseases or conditions. For example, chlorite has been used to treat infections and to cause regeneration of bone marrow. See, for example, U.S. Pat. Nos. 4,725,437 and 4,851,222. Chlorite has also been used to treat HIV, recurrent prostate cancer, cystitis, and chronic active hepatitis C disease. See, for example, McGrath et al., Development of WF10, a novel macrophage-regulating agent, *Curr Opin Investig Drugs*, 3(3):365-73 (March 2002). These diseases or conditions have generally been treated with intravenous injection of WF10, a commercially available formulation of chlorite. The approximately 12.3 pH of this formulation may be problematic for some forms of administration to physiological systems.

Chlorite has also been described for use in treating oral or periodontal diseases or conditions, such as inflammation of the gingiva. See, for example, U.S. Pat. No. 6,350,438.

Earlier formulations of chlorite include tetrachlorodecaoxygen, or TCDO, preparations by Kuhne, which are described in greater detail in U.S. Pat. No. 4,507,285 and below; and formulations including inorganic boron, such as those described in U.S. Pat. No. 4,296,103 to Laso; chlorite formulations are also disclosed in, for example, U.S. Pat. No. 3,082,146.

TCDO, which is also known as OXO-K993, is one form of stabilized chlorite. It is available from OxoChemie GmbH (Wanzleben, Germany). OXO-K993 is a mixture of chlorite, chloride, chlorate, and sulfate ions. WF10 is a dilution of TCDO intravenously administered to treat, for example, HIV/AIDS and cancer. Oxoferin is a more dilute form of OXO-K993 which has been used for topical wound healing. All of these formulations comprise chlorite ion, chloride ion, chlorate ion, and sulfate ion. For example, according to the WF10 packaging information, after dilution WF10 contains 4.25% chlorite ions, 1.9% chloride ions, 1.5% chlorate ions, 0.7% sulfate ions, and sodium as the cation (percentages in weight/total volume). The non-chlorite elements of TCDO in these various forms, for example the chlorate ions, may cause undesirable effects when administered to physiological systems. For example, ingestion of sodium chlorate causes irritation to the gastrointestinal tract, and may result in nausea, vomiting and diarrhea. Mallinckrodt Baker Inc. MSDS S3314, Aug. 10, 2004. Other symptoms include abdominal pain, hemolysis, methemoglobinemia, cyanosis, anuria, coma, and convulsions. Id. Further, exposure to sodium chlorate may cause liver and kidney damage, and repeated ingestion of small amounts may cause loss of appetite and weight loss. Id.

Various topically formulated chlorite-containing gums, toothpastes, lozenges, etc., have been developed. See, for example, U.S. Pat. No. 6,350,438 and related patents and applications. However, these topical, oral formulations are not appropriate for many uses, including but not limited to nontopical uses such as parenteral or systemic administration.

Thus, there remains a need for chlorite formulations that are better suited to administration to physiological systems, including but not limited to parenteral and systemic administration to physiological systems.

SUMMARY OF THE INVENTION

In general, in one aspect the invention provides an aqueous formulation including an aqueous solvent, chlorite and a pH-adjusting agent. In some embodiments formulation includes a weight ratio of chlorite:chlorate that is greater than 100:1.5, greater than 100:0.5. In one embodiment the formulation is substantially free of chlorate.

Some embodiments provide a formulation wherein the weight ratio of chlorite:sulfate is greater than 100:16.4, or greater than 100:1.6. In another embodiment the formulation is substantially free of sulfate.

In another embodiment the formulation includes a weight ratio of chlorite:chloride that is greater than 100:10.

In certain embodiments the pH of the formulation is between about 7.0 and about 11.5, or between about 7.0 and 8.5.

In one embodiment the pH adjusting agent is a phosphate or an acetate. In a particular embodiment the pH adjusting agent is monosodium phosphate.

In one embodiment the formulation includes a percent by weight of chlorite that is between about 0.5% and about 5% in the formulation. In one embodiment the concentration of chlorite in the formulation is between about 50 mM and about 100 mM.

In general, in one aspect the invention provides an aqueous formulation including chlorite, sodium, phosphate, and water, wherein the formulation has a pH between about 7.0 and about 11.5, and wherein the formulation comprises a weight ratio of chlorite:chlorate of greater than 100:0.5. In one embodiment the formulation is comprised essentially of chlorite, sodium, phosphate, and water. In one embodiment the concentration of chlorite is between about 50 mM and about 70 mM chlorite.

In general, in one aspect the invention provides an aqueous formulation includes chlorite and an aqueous solvent, wherein the formulation shows one or more indicia of a diminished non-specific toxicity relative to the same concentration of chlorite formulated as WF10 in an in vitro assay.

In general, in one aspect the invention provides an aqueous formulation including chlorite and an aqueous solvent, wherein the formulation shows one or more indicia of diminished toxicity when systemically administered to a subject, relative to the toxicity of the same concentration of chlorite formulated as WF10, when systemically administered to a subject. In one embodiment the toxicity is one or more of asthenia, injection site reaction, or injection site pain.

In general, in one aspect the invention provides a pharmaceutical composition including: (a) chlorite; (b) a pH adjusting agent; and (c) a pharmaceutically acceptable excipient. In one embodiment the composition has a weight ratio of chlorite:chlorate of greater than 100:1.5. In a particular embodiment the excipient includes water.

In general, in one aspect the invention provides a method of administering chlorite to a subject, wherein the method includes parenterally administering to a subject in need thereof a therapeutically effective amount of an aqueous formulation comprising an aqueous solvent, a pH adjusting agent and chlorite. In one embodiment the weight ratio of chlorite:chlorate is greater than 100:1.5. In another embodiment the formulation is administered intravenously.

In general, in one aspect the invention provides a unit dose form of a formulation, wherein the unit dose form comprises an effective amount of a pharmaceutical composition including: (a) chlorite; (b) a pH adjusting agent; and (c) a pharmaceutically acceptable excipient. In one embodiment the unit dose is ready for administration to a subject. In another embodiment the unit dose is diluted prior to administration to a subject. In one embodiment the pH of the composition is between about 7.1 and about 7.7.

In general, in one aspect the invention provides a method of preparing a formulation including chlorite, wherein the method includes: (a) concentrating a chlorite solution at a temperature between 60° C. to about 100° C., whereby impurities precipitate from the solution; (b) removing the impurities from the concentrated solution by filtration; (c) inducing crystallization of chlorite from the concentrated solution by freezing; (d) harvesting the resulting chlorite solids by filtration; and (e) dissolving the chlorite solids in an aqueous solvent. In one embodiment the temperature in step (a) is between 65° C. to about 80° C. In one embodiment the temperature in step (a) is about 70° C. In another embodiment the step (a) is carried out under reduced pressure. In another embodiment the inducing crystallization of chlorite in step (c) includes cooling the concentrated chlorite solution to a temperature no greater than about 10° C. In yet another embodiment the concentrated chlorite solution is cooled to a temperature between about 20° C. to about 30° C. In a particular embodiment the concentrated chlorite solution is cooled to a temperature of 25° C. In one embodiment the filtration in step (d) is centrifugal filtration. In one embodiment the invention provides a chlorite composition prepared by the described method.

In general, in one aspect the invention provides a method of preparing a formulation comprising chlorite and an aqueous solvent, wherein the method includes: (a) adjusting the pH of the formulation to between about 7 and about 11.5 with a pH modifying agent, wherein the pH modifying agent does not subject the chlorite to high local acidity, wherein the resulting formulation is substantially free of one or more of a member from the group consisting of chlorate or sulfate ions. In one embodiment the resulting formulation is substantially free of chlorate. In another embodiment the formulation is substantially free of sulfate. In one embodiment the pH is adjusted to about 7.4. In a particular embodiment the pH modifying agent is monosodium phosphate. In one embodiment step (a) includes adding the pH adjusting agent to an aqueous mixture of chlorite and aqueous solvent. In one embodiment the invention provides a chlorite composition prepared by the described method.

In general, in one aspect the invention provides a method of preparing a formulation comprising chlorite, wherein the method includes: (a) adjusting the pH of an aqueous solution comprising chlorite with a pH modifying agent, and wherein the resulting formulation is substantially free of one or more of chlorate or chlorine dioxide. In one embodiment the method includes before step (a), the step of purifying the chlorite. In one embodiment the pH is adjusted to between about 7.0 and about 11.5. In another embodiment the pH is adjusted to between about 7.0 and about 8.5. In a particular embodiment the pH is adjusted to about 7.4. In one embodiment the pH modifying agent is monosodium phosphate. In one embodiment the resulting formulation is substantially free of chlorate. In another embodiment the resulting formulation is substantially free of chlorine dioxide. In one embodiment step (a) includes adding chlorite or an aqueous mixture thereof to a solution of phosphate buffer. In one embodiment the phosphate buffer is monosodium phosphate. In a further embodiment step (a) comprises adding the pH adjusting agent to an aqueous mixture of chlorite and aqueous solvent.

In a related embodiment purifying comprises the steps of: (a) concentrating a chlorite solution at a temperature between 60° C. to about 100° C., whereby impurities precipitate from the solution; (b) removing the impurities from the concentrated solution by filtration; (c) inducing crystallization of chlorite from the concentrated solution by freezing; (d) harvesting the resulting chlorite solids by filtration; and (e) dissolving the chlorite solids in an aqueous solvent. In one embodiment the temperature in step (a) is between 65° C. to about 80° C. In another embodiment the temperature in step (a) is about 70° C. In one embodiment the step (a) is carried out under reduced pressure. In one embodiment inducing crystallization of chlorite in step (c) includes cooling the concentrated chlorite solution to a temperature no greater than about 10° C. In one embodiment the concentrated chlorite solution is cooled to a temperature between about 20° C. to about 30° C. to induce crystallization. In a particular embodiment the concentrated chlorite solution is cooled to a temperature of 25° C. to induce crystallization. In one embodiment the filtration in step (d) is centrifugal filtration. In one embodiment the invention provides a chlorite composition prepared by the described method.

In general, in one aspect the invention provides a method of treating a disease or disorder comprising administering to a subject in need thereof an effective amount of a pharmaceutical composition including: (a) chlorite; (b) a pH adjusting agent; and (c) a pharmaceutically acceptable excipient. In one embodiment the disease or disorder is one or more of infection, bone marrow degradation, neoplasia, cystitis, HIV, chronic hepatitis C disease, oral disease, periodontal disease, inflammation of the gingiva, topical wounds, multiple sclerosis and a neurodegenerative disease or disorder. In another embodiment the disease is a neoplasia selected from one or more of bladder cancer, melanoma, breast cancer, non-Hodgkin's lymphoma, colon and rectal cancer, pancreatic cancer, endometrial cancer, prostate cancer, kidney (renal cell) cancer, skin cancer (non-melanoma), leukemia, thyroid cancer and lung cancer. In one embodiment the disease or disorder is a neurodegenerative disease or disorder. In a particular embodiment the neurodegenerative disease or disorder is a macrophage-associated neurodegenerative disease or disorder. In one embodiment the neurodegenerative disease or disorder is ALS. In another embodiment the neurodegenerative disease or disorder is Alzheimer's disease. In a further embodiment the neurodegenerative disease or disorder is Parkinson's disease.

In general, in one aspect the invention provides a business method including preparing an item of any of aspects of the invention as described above, according to a GMP protocol.

In general, in one aspect the invention provides a aqueous formulation including an aqueous solvent and chlorite, wherein the formulation is produced using a GMP protocol. In one embodiment the formulation further includes a weight ratio of chlorite:chloride greater than 100:10. In another embodiment the ratio of chlorite:chlorate is greater than 100:0.5. In another embodiment the chlorite comprises a purity greater than 80%, greater than 85%, greater than 90%, greater than 95% or greater than 99%. In general, in one aspect the invention provides aqueous formulations of chlorite, an aqueous solvent and a pH adjusting agent, as described further herein, as well as pharmaceutical formulations of the foregoing, kits, methods for making the formulations, and methods for using the formulations, including the pharmaceutical formulations described herein.

Unless the context makes clear, all percentages are weight per total volume percentages.

In one aspect are provided aqueous formulations comprising chlorite, an aqueous solvent, and a pH adjusting agent, wherein the formulation has a pH of about 7 to about 11.5, and wherein the formulation comprises a member from the group consisting of, or alternatively any one or more of: no greater than about 1.8% chloride, no greater than about 1.4% of chlorate, and no greater than about 0.6% sulfate. In some embodiments are provided aqueous formulations comprising chlorite, an aqueous solvent and a pH adjusting agent, wherein the formulation has a pH of about 7 to about 11.5, and wherein the formulation comprises a member from the group consisting of, or alternatively any one or more of: no greater than about 0.24% chloride, no greater than about 0.19% of chlorate, and no greater than about 0.08% sulfate. In some embodiments are provided aqueous formulations comprising chlorite, an aqueous solvent and a pH adjusting agent, wherein the formulation has a pH of about 7 to about 11.5, wherein the formulation comprises no greater than about 85% of the amount of a member of the group consisting of, or alternatively any one or more of chlorate and sulfate when compared to an equal weight/volume percent of chlorite formulated as WF10.

In some embodiments, any of the formulations or pharmaceutical formulations described herein comprise a pH adjusting agent that comprises phosphate. In some embodiments, any of the formulations or pharmaceutical formulations described herein comprises a pH adjusting agent that consists essentially of phosphate. In some embodiments, any of the formulations or pharmaceutical formulations described herein comprise a pH adjusting agent that comprises acetic acid. In some embodiments, any of the formulations or pharmaceutical formulations described herein comprise a pH adjusting agent that consists essentially of acetic acid.

In a further aspect are provided methods of administering chlorite to a subject, wherein the method comprises administering a therapeutically effective amount of any of the formulations or pharmaceutical formulations described herein to a subject in need thereof. In some embodiments, the formulations or pharmaceutical formulations are administered parenterally. In some embodiments, the formulations or pharmaceutical formulations are administered systemically. In some embodiments, the formulations or pharmaceutical formulations are administered intravenously. In some embodiments, the formulations or pharmaceutical formulations are administered non-topically.

Described herein are methods of administering chlorite to a subject, wherein the method comprises intravenously administering a therapeutically effective amount of an aqueous pharmaceutical formulation comprising chlorite, an aqueous solvent, a pH adjusting agent, and a saline solution, wherein the formulation has a pH of about 7 to about 11.5, wherein the formulation comprises no greater than about 85% of the amount of a member of the group consisting of, or alternatively any one or more of, chlorate and sulfate when compared to the same percent of chlorite formulated as WF10. In some embodiments, the formulation administered has a pH of about 7.0 to about 10. In some embodiments, the formulation has a pH of about 7.0 to about 9.0. In some embodiments, the formulation administered has a pH of about 7.0 to about 8.5. In some embodiments, the formulation administered has a pH of about 7.1 to about 7.7. In some embodiments, the method comprises intravenously administering a therapeutically effective amount of a liquid pharmaceutical formulation comprising chlorite, an aqueous solvent, saline, and a pH adjusting agent, wherein the formulation has a pH of about 7.1 to about 7.7, wherein the formulation comprises no greater than about 0.6% of sulfate ions or 1.4% of chlorate ions, wherein the concentration of chlorite is between about 2 and about 3 mM. In some embodiments, the method comprises intravenously administering a therapeutically effective amount of a liquid pharmaceutical formulation comprising chlorite, an aqueous solvent, saline, and a pH adjusting agent, wherein the formulation has a pH of about 7.1 to about 7.7, wherein the formulation comprises no greater than about 0.08% of sulfate ions or 0.19% of chlorate ions, wherein the concentration of chlorite is between about 2 and about 3 mM.

Described herein are methods of administering chlorite to a subject, wherein the method comprises intravenously administering a therapeutically effective amount of an aqueous pharmaceutical formulation comprising chlorite, an aqueous solvent, and a saline solution, wherein the formulation comprises no greater than about 85% of the amount of a member of the group consisting of, or alternatively any one or more of, chlorate and sulfate when compared to the same percent of chlorite formulated as WF10. In some embodiments, the method comprises intravenously administering a therapeutically effective amount of a liquid pharmaceutical formulation comprising chlorite, an aqueous solvent, and saline, wherein the formulation comprises no greater than about 0.6% of sulfate ions or 1.4% of chlorate ions, wherein the concentration of chlorite is between about 2 and about 3 mM. In some embodiments, the method comprises intravenously administering a therapeutically effective amount of a liquid pharmaceutical formulation comprising chlorite, an aqueous solvent, and saline, wherein the formulation comprises no greater than about 0.08% of sulfate ions or 0.19% of chlorate ions, wherein the concentration of chlorite is between about 2 and about 3 mM.

In an additional aspect, provided are methods of treatment comprising administering a formulation or pharmaceutical formulation described herein in a therapeutically effective amount to a subject in need thereof, to treat one or more of the diseases or conditions for which chlorite is presently used, including but not limited to those diseases or conditions described herein. In some embodiments, the method of treatment is to treat one or more of the diseases or conditions described herein.

In a further aspect are provided use of the formulations or pharmaceutical formulations of chlorite as described herein in the manufacture of a medicament. Particularly, the manufacture of a medicament for use in the treatment of conditions as described herein. Further, the pharmaceutical formulations thereof, variously described herein, are also intended for use in the manufacture of a medicament for use in treatment of the conditions and, in accordance with the methods, described herein, unless otherwise noted.

In an additional aspect, provided herein are unit dose forms of a formulation, wherein the unit dose form comprises an effective amount of any of the formulations or pharmaceutical formulations described herein.

In a further aspect, provided herein are kits comprising one or more unit dose forms as described herein. In some embodiments, the kit comprises one or more of packaging and instructions for use to treat one or more diseases or conditions. In some embodiments, the kit comprises a diluent in a separate compartment from the formulation or pharmaceutical formulation. In some embodiments, the kit comprises a diluent in a separate container from the formulation or pharmaceutical formulation. In some embodiments, the kit comprises a diluent which is not in physical contact with the formulation or pharmaceutical formulation. In some embodiments, the kit comprises any of one or more unit dose forms described herein in one or more sealed vessels. In some embodiments, the kit comprises any of one or more sterile unit dose forms.

In a further aspect, provided herein are methods of preparing any of the formulations or pharmaceutical formulations described herein.

Described herein are methods of preparing a formulation comprising chlorite and an aqueous solvent as described herein, wherein step (a) comprises adding chlorite or an aqueous mixture thereof to a solution of a physiologically compatible buffer. A "physiologically compatible" buffer is a buffer with a level of its constituent components that is generally accepted by those of skill in the art as appropriate for use in the subject being treated. In some embodiments, the buffer is a phosphate buffer.

Described herein are methods of preparing a formulation comprising chlorite and an aqueous solvent as described herein, wherein step (a) comprises adding the pH adjusting agent to an aqueous mixture of chlorite and an aqueous solvent.

Described herein are methods of preparing a formulation comprising chlorite as described herein, wherein the resulting formulation is substantially free of chlorate.

Described herein are methods of preparing a formulation comprising chlorite as described herein, wherein the resulting formulation is substantially free of chlorine dioxide.

Unless otherwise noted, it is intended that the formulations, including the pharmaceutical formulations, described herein may be used in the methods and kits described herein. As used herein, embodiments described with elements "selected from the group consisting of" also contemplate alternative embodiments which are "any one or more of." As used herein, embodiments described as "no greater than" an element, also contemplate alternative embodiments which are "less than about" those elements. Further, aspect and embodiments of the invention described herein also contemplate "consisting" and/or "consisting essentially of" aspects and embodiments.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
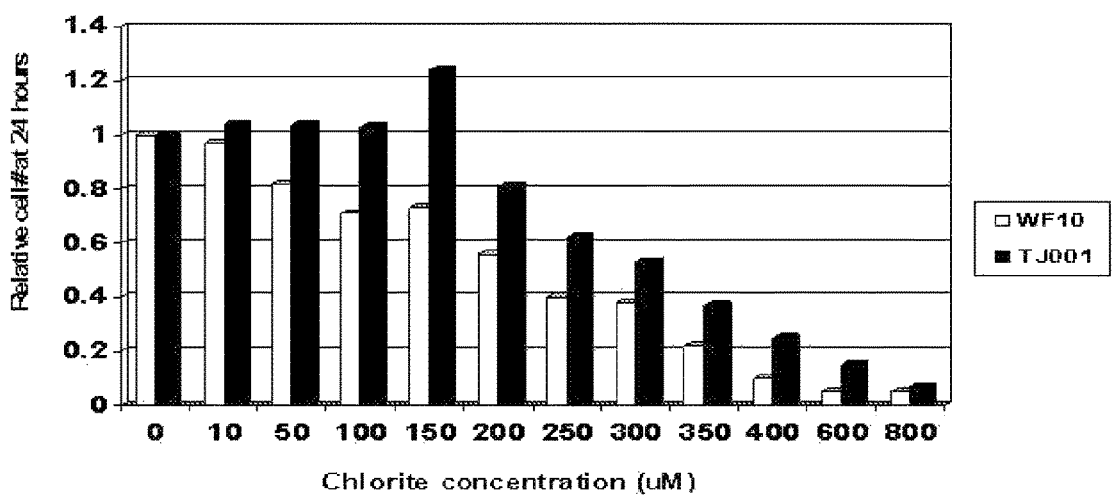
FIG. 1 depicts the relative nonspecific toxicity of a chlorite formulation described in Example 4 versus WF10 in a Jurkat T-cell cell line.

Described herein are chlorite formulations, including but not limited to pharmaceutical formulations, better suited to administration to physiological systems than those previously described, wherein the formulations are suitable for various modes of administration, including but not limited to non-topical, parenteral, systemic, or intravenous administration. In some variations the chlorite formulations described herein have a pH that is closer to physiological pH than those of previous chlorite formulations. In some variations, the chlorite formulations described herein do not have the impurities or deleterious non-chlorite elements of previously described chlorite formulations. In some variations, the chlorite formulations described herein are less toxic to physiological systems than those previously described. Also described herein are methods of treatment of various diseases or conditions described herein. Also described herein is the use of the chlorite formulations and pharmaceutical formulations described herein in the manufacture of a medicament to treat the diseases or conditions described herein.

In certain aspects, this invention provides formulation of chlorite in aqueous solution in which the chlorite is 97-99% pure. As used herein, the "purity" of chlorite in a sample is calculated as the percent weight of chlorite salt to the total weight of the sample. In determining the purity of chlorite in a solution, the weight of the solvent (e.g., water in an aqueous solution) is not included. Purity may be evaluated using ion chromatography and an ion detector, by calibrated integration of the respective peaks; for example, chlorite, chloride, chlorate, phosphate and sulfate in the compound or formulation. For example, chlorite is commercially available as sodium chlorite, technical grade, at a purity of 80% (catalog No. 244155 Sigma-Aldrich).

This invention further provides compositions of this invention have reduced amounts of chlorate, sulfate or chloride compared with commercially available chlorite compositions. As used herein, a formulation is "substantially free" of a molecule if the molecule comprises no more than 1 part in 1000 per weight of non-solvent molecules in the formulation. In certain embodiments, the weight ratio of chlorite to chlorate is greater than 100:1.5, greater than 100:0.5, greater than 100:1, or greater than 100:0.1. In one embodiment the composition is substantially free of chlorate. In another embodiment, the weight ratio of chlorite to chloride greater than 100:45.5 or greater than 100:8.5. In one embodiment the composition is substantially free of chloride. In a further embodiment, the weight ratio of chlorite to sulfate is greater than 100:16.4 or greater than 100:1.6. In one embodiment the composition is substantially free of sulfate.

Described herein are methods of adjusting the pH of a chlorite formulation to between about 7 and about 11.5. In some variations, the pH of a chlorite formulation is lowered to between about 7 and about 11.5 using a pH adjusting compound that does not expose the formulation to high local acidity. In some variations the pH adjusting compound is any one or more of monosodium phosphate, or acetic acid. Described herein are methods of adjusting the pH of a chlorite formulation to no greater than about 11.5.

Also described herein are methods of preparing chlorite formulations and pharmaceutical formulations, including but not limited to the chlorite formulations specifically described herein. Also described herein are kits and methods of administration of the formulations and pharmaceutical formulations described herein. Various exemplary aspects and variations of the invention are described in the "Brief Summary of the Invention," as well as elsewhere herein, including but not limited to the Examples. It is also understood that the invention includes embodiments comprising, consisting essentially of, and/or consisting of one or more elements as described herein.

Formulations

Described herein are aqueous formulations comprising chlorite. In some variations, the chlorite formulation comprises an aqueous solvent, and optionally one or more other solvents for chlorite. Described herein are formulations comprising chlorite and an aqueous solvent for chlorite, the formulations having a pH of about 7 to about 11.5.

Solvents or combinations of solvents for use in the formulations described herein can be determined by a variety of methods known in the art. One nonlimiting example includes (1) theoretically estimating solvent solubility parameter value(s) and choosing the one(s) that match with chlorite, using standard equations in the field; and (2) experimentally determining the saturation solubility of chlorite in the solvent(s), and (3) choosing one or more that exhibits the desired solubility, and (4) selecting a solvent or solvents that do not diminish the activity of chlorite, or that do not or only minimally react with chlorite. In some variations, the liquid formulations described herein comprise a plurality of solvents.

In some variations, the chlorite formulations described herein comprise an aqueous solvent. In some variations, water is the principal solvent in the aqueous formulations described herein. In some variations, water is at least about 50% by volume of the solvent component of an aqueous formulation. In some variations, water is at least about 50% by volume of the aqueous formulation. In some variations, water is any of between about 50 to about 60, between about 60 to about 70, between about 70 to about 80, between about 80 to about 90, between about 90 to about 99, at least about 50, at least about 60, at least about 70, at least about 80, at least about 90, or at least about 95, about 50, about 60, about 70, about 80, about 90, or about 95 percent by volume of the solvent component. In some variations, water is any of between about 50 to about 60, between about 60 to about 70, between about 70 to about 80, between about 80 to about 90, between about 90 to about 99, at least about 50, at least about 60, at least about 70, at least about 80, at least about 90, or at least about 95, percent by volume of the aqueous formulation. In some variations, water is at least about 95% by volume of the aqueous formulation. In some variations, water is between about 80 to about 90% by volume of the aqueous formulation. In some variations, water is between about 90 to about 99% by volume of the aqueous formulation.

The formulations may have differing concentration of chlorite. In some embodiments the concentration of chlorite in the formulation is high, and then is diluted to a less concentrated form prior to administration. In some embodiments, a formulation described herein is diluted any of about 2.5×, about 5×, about 7.5×, about 10×, about 20×, about 25×, about 50×, about 100×, about 200×, about 250×, about 300×, about 500×, or about 1000×. In some embodiments, a formulation described herein is diluted about 2.5×, about 5×, about 10×, about 20×, about 25×, about 50×, about 100×, about 200×, about 250×, about 300×, about 500×, about 1000×; between about 2× and about 10×, between about 10× and about 50×, between about 50× and about 100×, between about 100× and about 500×, or between about 500× and about 1000×. In some embodiments, a formulation as described herein is diluted between about 2× and about 10×. In some embodiments, a formulation as described herein is diluted between about 10× and about 50×. In some embodiments, a formulation as described herein is diluted about 7.5×. In some embodiments, a formulation as described herein is diluted about 25×. In some embodiments, a formulation as described herein is diluted about 200×. In some variations, the concentration of chlorite in the formulations described herein is between about 1 µM and about 1.5 M. In another variation, the concentration of chlorite in the formulations described herein is between any of about 1 M and about 1.5 M; between about 1 µM and about 100 mM; between about between about 10 µM and about 100 mM; between about 0.1 mM and about 10 mM; between about 0.1 mM and about 500 mM; between about 0.1 mM and about 200 mM; between about 1 mM and about 100 mM; between about 0.1 mM and about 5 mM; between about 50 mM and about 100 mM; between about 55 mM and about 70 mM; between about 60 mM and about 65 mM; between about 100 mM and about 500 mM; between about 200 mM and about 400 mM; between about 300 mM and about 700 mM; about 1 mM; about 1.5 mM; about 2 mM; about 2.5 mM; about 3 mM; about 3.5 mM; about 4 mM; about 5 mM; about 10 mM; about 20 mM; about 30 mM; about 40 mM; about 50 mM; about 60 mM; about 62 mM; about 65 mM; about 70 mM; about 80 mM; about 90 mM; about 100 mM; at least about 0.1 mM; at least about 1 mM; at least about 2 mM; at least about 5 mM; at least about 10 mM; at least about 20 mM; at least about 30 mM; at least about 40 mM; at least about 50 mM; at least about 60 mM; at least about 70 mM; at least about 80 mM; at least about 90 mM; or at least about 100 mM. In some variations, the concentration of chlorate in the formulations described herein is between about 50 mM and about 100 mM. In some variations, the concentration of chlorate in the formulations described herein is between about 55 mM and about 75 mM. In some variations, the concentration of chlorate in the formulations described herein is between about 0.1 mM and about 10 mM. In some variations, the concentration of chlorate in the formulations described herein is between about 1 mM and about 5 mM.

In some variations, the chlorite formulation has a pH no greater than about 12.0. In some variations, the pH of the formulation is any of no greater than about 11.5, about 11.0, about 10.5, about 10.0, about 9.5, about 9.0, about 8.5, about 8.0, about 7.5, about 7.0, about 6.5, or about 6.0. In some variations, the pH of the formulation is no greater than about 11.5. In some variations, the pH of the formulation is no greater than about 10.5. In some variations, the pH of the formulation is no greater than about 8.5. In some variations, the pH of the formulation is no greater than about 7.5. In some variations, the pH of the formulation is between any one or more of about 7 and about 12; between about 7 and about 11.5; between about 7 and about 10.5; between about 7 and about 10; between about 7 and about 9.5; between about 7 and about 9.0; between about 7 and about 8.5; between about 7 and about 8.0; between about 7 and about 7.5; between about 7.5 and about 8; between about 7.5 and about 8.5; between about 7 and about 8; between about 8 and about 9; between about 7.0 and about 8.5; between about 8 and about 8.5; between about 8.5 and about 9; between about 7.1 and about 7.7; between about 7.2 and about 7.6; between about 7.3 and about 7.4; about 7.0; about 7.1; about 7.2; about 7.3; about 7.4; about 7.5; about 7.6; about 7.7; about 7.8; about 7.9; about 8.0; about 8.1; about 8.2; about 8.3; about 8.4; about 8.5; about 8.6; about 8.7; about 8.8; or about 8.9. In some variations, the chlorite formulation has a pH of about 7.0 to about 9.0. In some variations, the chlorite formulation has a pH of about 7.0 to about 8.5. In some variations, the chlorite formulation has a pH of about 6.0 to about 8.5. In some variations, the chlorite formulation has a pH of about 7.0 to about 8.0. In some variations, the chlorite formulation has a pH of about 7.4.

In some variations, the formulations described herein have a pH as described above, and is formulated for any one or more of parenteral, systemic, or intravenous administration.

In some variations, the formulations described herein have a pH as described above, and have a percentage chlorite purity as described herein.

In some variations, the formulations described herein have a pH as described above, and have a concentration of chlorite as described herein. In some embodiments, the aqueous formulations described herein have a pH between about 7 and about 11.5, or between about 7.0 and about 10, or between about 7.0 and about 9.0, or between about 7.0 and about 8.5, or between about 7.1 and about 7.7, and have a concentration of chlorite between about 1 and about 100 mM. In some embodiments, the aqueous formulations described herein have a pH between about 7 and about 11.5, or between about 7.0 and about 10, or between about 7.0 and about 9.0, or between about 7.0 and about 8.5, or between about 7.1 and about 7.7, and have a concentration of chlorite between about 1 and about 5 mM. In some embodiments, the aqueous formulations described herein have a pH between about 7 and about 11.5, or between about 7.0 and about 10, or between about 7.0 and about 9.0, or between about 7.0 and about 8.5, or between about 7.1 and about 7.7, and have a concentration of chlorite between about 50 and about 80 mM.

In some embodiments, the aqueous formulations described herein have a pH between about 7 and about 11.5, or between about 7.0 and about 10, or between about 7.0 and about 9.0, or between about 7.0 and about 8.5, or between about 7.1 and about 7.7, wherein the pH was adjusted with a pH adjusting agent that is any one or more of a phosphate, or acetic acid.

In some variations, the formulations described herein are stable with respect to one or more of pH or chlorite degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In some variations, the formulations described herein are stable with respect to one or more of pH or chlorite degradation over a period of any of at least about 1 week. Described herein are stable with respect to one or more of pH or chlorite degradation over a period of any of at least about 1 month. In some variations, the formulations described herein are stable with respect to one or more of pH or chlorite degradation at one or more of room temperature, refrigerated conditions, or approximately 4° C. In some variations, the formulations described herein are stable with respect to one or more of pH or chlorite degradation under conditions of diminished light or storage in a container that limits the amount of light to which the formulation is subjected. In some variations, the formulations described herein are stable with respect to one or more of pH or chlorite degradation when stored in the dark. Examples of stable pH, as used herein, means that the pH of the formulation changes by less than any of about 0.1, about 0.2, about 0.3, about 0.4, about 0.5, about 0.6, about 0.7, about 0.8, about 0.9, or about 1 relative to the pH of the formulation as initially prepared. In some variations, the pH of the formulation changes by less than about 0.2 relative to the pH of the formulation as initially prepared. The pH may be measured using, for example, a pH meter. Examples of stable chlorite formulations include those in which less than any of about 0.1%, less than about 0.2%, less than about 0.3%, less than about 0.4%, less than about 0.5%, less than about 0.6%, less than about 0.7%, less than about 0.8%, less than about 0.9%, less than about 1%, less than about 2%, less than about 3%, less than about 4%, less than about 5%, less than about 6%, less than about 7%, less than about 8%, less than about 9%, or less than about 10% of the chlorite degrades into a non-chlorite ion relative to the amount of chlorite present in the formulation as initially prepared. In some variations, less than about 2% of the chlorite degrades into a non-chlorite compound relative to the amount of chlorite present in the formulation as initially prepared. In some variations, less than about 0.5% of the chlorite degrades into a non-chlorite compound relative to the amount of chlorite present in the formulation as initially prepared. The presence of non-chlorite elements may be measured, for example, using gas chromatography (GC), mass spectrometry, or other methods known by those of skill in the art.

In some variations, the chlorite formulations described herein comprise no greater than about 5% by weight of deleterious non-chlorite elements of other commercially available formulations. In some variations, the chlorite formulations described herein comprise any of no greater than about 4%, about 3%, about 2%, about 1%, about 0.5%, about 0.3%, about 0.25%, about 0.2%, about 0.1%, about 0.05%, or about 0.02%, by weight of deleterious non-chlorite elements of other commercially available formulations. In some variations, the chlorite formulations described herein comprise any of no greater than about 4% by weight of deleterious non-chlorite elements of other commercially available formulations. In some variations, the chlorite formulations described herein comprise any of no greater than about 2% by weight of deleterious non-chlorite elements of other commercially available formulations. In some variations, the chlorite formulations described herein comprise any of no greater than about 0.5% by weight of deleterious non-chlorite elements of other commercially available formulations. In some variations, the chlorite formulations described herein comprise any of no greater than about 0.05% by weight of deleterious non-chlorite elements of other commercially available formulations. In some variations, the chlorite formulations described herein are substantially free of the deleterious non-chlorite elements of other commercially available formulations. Nonlimiting examples of methods of detection of non-chlorite components include HPLC; SPCS, for example using a Novosep A2 column with 3.6 mM Sodium Carbonate as a mobile phase, 5µ, 250×4.0 mm, flow rate 0.8 mL/min; DS-Plus Suppressor, for example using a Novosep A2 column with 3.6 mM Sodium Carbonate as a mobile phase, 5µ, 250×4.0 mm, flow rate 0.8 mL/min; an Allsep A-2 Anion column using 2.1 mM NaHCO3/1.6 mM Na2CO3 as a mobile phase, 100×4.6 mm, flow rate 2.0 mL/min; an anion HC column using 2.8 mM NaHCO3:2.2 mM Na2CO3 in 10% Methanol as a mobile phase, 150×4.6 mm, flow rate 1.4 mL/min; or an Allsep A-2 Anion column using 2.1 mM NaHCO3/1.6 mM Na2CO3 as a mobile phase, 5µ, 100×4.6 mm, flow rate 1.0 mL/min. See, for example, the Alltech Associates, Inc. Grace Davison line of products and product information for details. In some variations, formulations described herein comprise no greater than about 10%, about 20%, about 30%, about 40%, about 50%, about 60%, about 70%, about 75%, about 80%, about 85%, about 90%, or about 95% of the amount of a member of the group consisting of, or alternatively any one or more of, chlorate ions and sulfate ions present in an equal weight/volume percent of chlorite formulated as WF10 or a dilution thereof. That is, in some embodiments, when a non-WF10 formulation as described herein comprises a certain percent w/v of chlorite, such formulation has no greater than about the stated percentage of the amount of one or more of the specified non-chlorite components in WF10 or a dilution thereof, wherein the WF10 or dilution thereof comprises the same percent w/v of chlorite as is found in the non-WF10 formulation with which it is being compared. In some embodiments, the formulations described herein comprise no greater than about 75% of the amount of a member of the group consisting of, or alternatively any one or more of, chlorate ions and sulfate ions present in an equal weight/volume percent of chlorite formulated as WF10. In some embodiments, the formulations described herein comprise no greater than about 85% of the amount of a member of the group consisting of, or alternatively any one or more of, chlorate ions and sulfate ions present in an equal weight/volume percent of chlorite formulated as WF10. In some embodiments, the formulations described herein comprise no greater than about 50% of the amount of a member of the group consisting of, or alternatively any one or more of, chlorate ions and sulfate ions present in an equal weight/volume percent of chlorite formulated as WF10.

It can be understood from the product insert of WF10 that WF10 reportedly includes a ratio of chlorite to chlorate of 100:35.7 (4.25% to 1.5%), a ratio of chlorite to chloride of 100:45.5 (4.25% to 1.9%) and a chlorite to sulfate ratio of 100:16.4 (4.25% to 0.7%).

Examples of deleterious non chlorite components include non-chlorite components that cause an adverse reaction when administered to physiological systems. In some variations, a deleterious non chlorite component is associated with one or more indicia of toxicity in one or more of in vitro or in vivo assays known in the art, or are associated with one or indicia of toxicity when administered to a physiological system, including but not limited to a subject, including but not limited to a human subject. Deleterious non chlorite components include but are not limited to sulfate, chlorine dioxide, chlorate, and borate. In some variations, the chlorite formulations described herein are substantially free of the deleterious non-chlorite elements of WF10. In some variations, the chlorite formulations described herein are substantially free of sulfate and chlorate ions.

In some variations, the chlorite formulations described herein contain less than about 1.9% of chloride ions. In some variations, the chlorite formulation contains any of less than about 1.9%, less than about 1.8%; less than about 1.5%; less than about 1.0%; less than about 0.5%; less than about 0.3%; less than about 0.1%; less than about 0.05%; less than about 0.01%; less than about 0.001%; between about 0.001 to about 0.1%; between about 0.1 to about 0.5%; between about 0.5 to about 1.0%; between about 1.0 to about 1.5%; or between about 1.5 to about 1.8% by weight of chloride ions. In some variations, the chlorite formulation contains less than about 0.5% by weight of chloride ions. In some variations, the chlorite formulation contains less than about 0.24% by weight of chloride ions. In some variations, the chlorite formulation contains less than about 0.2% by weight of chloride ions. In some variations, the chlorite formulation contains less than about 0.1% by weight of chloride ions. In some variations, the chlorite formulation is substantially free of chloride ions. In some variations, the level of chloride ions is below the level of detection using HPLC.

In some variations, the chlorite formulation contains less than about 1.5% of chlorate ions. In further variations, the chlorite formulation contains any of less than about 1.4%, less than about 1.3%; less than about 1.0%; less than about 0.5%; less than about 0.3%; less than about 0.1%; less than about 0.01%; less than about 0.001%; between about 0.001 to about 0.1%; between about 0.001 to about 0.01%; between about 0.01 to about 0.1%; between about 0.1 to about 0.5%; between about 0.5 to about 1.0%; or between about 1.0 to about 1.4% of chlorate ions. In some variations, the chlorite formulation is substantially free of chlorate ions. In some variations, the chlorite formulation contains less than about 0.5% by weight of chlorate ions. In some variations, the chlorite formulation is substantially free of chlorate ions. In some variations, the chlorite formulation contains less than about 0.19% by weight of chlorate ions. In some variations, the chlorite formulation contains less than about 0.1% by weight of chlorate ions. In some variations, the level of chlorate ions is below the level of detection using HPLC.

In some variations, the chlorite formulation contains less than about 0.7% of sulfate ions. In further variations, the chlorite formulation contains any of less than about 0.65%; less than about 0.6%; less than about 0.5%; less than about 0.4%; less than about 0.3%; less than about 0.2%; less than about 0.1%; less than about 0.08%; less than about 0.07%; less than about 0.06%; less than about 0.05%; less than about 0.005%; less than about 0.0005%; between about 0.001 to about 0.1%; between about 0.01 to about 0.1%; between about 0.01 to about 0.5%; between about 0.06 to about 0.08%; or between about 0.5 to about 0.65% of sulfate ions. In some variations, the chlorite formulation contains between about 0.5 to about 0.65% of sulfate ions. In some variations, the chlorite formulation is substantially free of sulfate ions. In some variations, the chlorite formulation contains less than about 0.5% by weight of sulfate ions. In some variations, the chlorite formulation is substantially free of sulfate ions. In some variations, the chlorite formulation contains less than about 0.08% by weight of sulfate ions. In some variations, the level of sulfate ions is below the level of detection using HPLC.

In some variations, the chlorite formulations described herein comprise phosphate ions. In some variations, the chlorite formulations described herein comprise sodium ions. In some variations, a chlorite formulation comprises chlorite, an aqueous solvent, sodium, and phosphate ions. In some variations, the aqueous solvent consists essentially of water. In some variations, a chlorite formulation consists essentially of chlorite, water, sodium, and phosphate, and is substantially free of chlorate. In some variations, a chlorite formulation consists essentially of chlorite, water, sodium, and phosphate, and is substantially free of chlorate, and further comprises a pharmaceutically acceptable diluent. In a further variation the pharmaceutically acceptable diluent is a saline solution.

In some variations, the chlorite formulations described herein comprise no greater than about 10% by weight of by products or impurities present in commercially available technical grade chlorite. Nonlimiting examples of by-products or impurities present in commercially available technical grade chlorite include chlorate, sulfate, chlorine dioxide, chloride, sodium bicarbonate, and sodium carbonate. In some variations, the chlorite formulations described herein comprise no greater than about any of 15%, about 12%, about 10%, about 9%, about 8%, about 7%, about 6%, about 5%, about 4%, about 3%, about 2%, about 1%, about 0.5%, about 0.3%, about 0.1%, between about 0.1 to about 5%; between about 5 to about 10%; or between about 10 to about 15% by weight of one or more degradation products or impurities present in commercially available technical grade chlorite, including but not limited to one or more of chlorate or sulfate. In some variations, the chlorite formulations described herein comprise no greater than about 0.5% by weight of degradation products or impurities present in commercially available technical grade chlorite, including but not limited to one or more of chlorate or sulfate. In some variations, the chlorite formulations described herein comprise no greater than about 5% by weight of degradation products or impurities present in commercially available technical grade chlorite, including but not limited to one or more of chlorate or sulfate. In some variations, the chlorite formulations described herein are substantially free of the degradation products or impurities present in commercially available technical grade chlorite, including but not limited to chlorate or sulfate.

In some variations, the formulations described herein are less toxic to a subject than previously reported chlorite formulations at the same concentration of chlorite, when administered by at least one of the routes of administration described herein, including but not limited to by non-topical, systemic, parenteral, or intravenous administration. In some variations, the toxicity of a chlorite formulation is analyzed for toxicity using an in vivo or in vitro toxicity assay, including well-known toxicity assays. In some variations the chlorite formulation is analyzed for toxicity using the non-specific in vitro toxicity assay in Example 4 below. In some variations, the formulations described herein exhibit a decreased non-specific toxicity relative to the same concentration of chlorite formulated as WF10 using the non-specific in vitro toxicity assay in Example 4 below. In some variations, a decreased non-specific toxicity is a lesser degree of cell death at the same concentration of chlorite using the non-specific in vitro toxicity assay in Example 4 below.

In another variation, toxicity is measured according to various response indicia of toxicity in a subject after administration of the chlorite formulations described herein, as compared to administration of other commercially available chlorite formulations. In some variations, toxicity is measured relative to systemic administration of chlorite formulated as WF10. In another variation, toxicity is measured relative to intravenous administration of chlorite formulated as WF10 to a subject. In some variations, toxicity is measured after administration to a mammalian subject, including but not limited to a human subject. In some variations, toxicity is measured as one or more of irritation to the surface to which the chlorite formulation is exposed, including but not limited to the gastrointestinal tract, nausea, vomiting, diarrhea, abdominal pain, hemolysis, methemoglobinemia, cyanosis, anuria, coma, convulsions, liver damage, kidney damage, loss of appetite, or weight loss. In some variations, toxicity is measured as one or more of asthenia, injection site pain, headache, rhinitis, or diarrhea. See, for example, McGrath M S, *Development Of WF10, A Novel Macrophage-Regulating Agent*, Curr Opin Investig Drugs, 3(3):365-73 (March 2002), which is incorporated by reference in its entirety. In another variation, toxicity is measured as anemia. Kempf et al., *Comparative Study On The Effects Of Chlorite Oxygen Reaction Product TCDO (Tetrachlorodecaoxygen) And Sodium Chlorite Solution (NaClO2) With Equimolar Chlorite Content On Bone Marrow And Peripheral Blood Of BDIX Rats*, Drugs Under Experimental and Clinical Research. 19(4):165-1 (1993). In some variations, toxicity is measured as asthenia. In some variations, toxicity is measured as injection site reaction. In some variations, toxicity is measured as injection site pain.

Pharmaceutical Formulations

Unless the context clearly indicates otherwise, any of the formulations described herein may be used in any of the pharmaceutical formulations described herein.

In some variations, the pharmaceutical formulations described herein are suitable for administration to a subject. By "suitable for administration to a subject" is meant that the pharmaceutical formulation, when obtained from a newly opened bottle and administered via the desired route, causes no greater than a clinically acceptable level of deleterious side effects.

In some embodiments, the formulations or pharmaceutical formulations described herein further comprise a saline solution. A saline solution, as used herein, refers to a physiologically acceptable solution with a physiologically acceptable level of sodium chloride. In some embodiments, the saline solution is isotonic.

Described herein are pharmaceutically acceptable chlorite formulations comprising one or more pharmaceutically acceptable excipients. Excipients, as used herein, refer to any non-chlorite, non-water, or non-saline element of a pharmaceutical formulation. Excipients include but are not limited to carriers, adjuvants, diluents, stabilizers, wetting agents, emulsifiers, buffers, preservatives, flavorings, inactive ingredients, gel formulations, erodible and non-erodible polymers, microspheres, liposomes, etc., including combinations of the foregoing, known to skilled artisans and described further herein. In some variations, the percent by weight of the excipient per the total volume of the formulation or pharmaceutical formulation is no greater than any of about 10%, about 9%, about 8%, about 7%, about 6%, about 5%, about 4%, about 3%, about 2%, about 1%, about 0.5%, about 0.4%, about 0.3%, about 0.2%, about 0.1%, or about 0.05%. In some variations, the percent by weight of the excipient per the total volume of the formulation or pharmaceutical formulation is no greater than about 1%. In some variations, the percent by weight of the excipient per the total volume of the formulation or pharmaceutical formulation is no greater than about 3%.

Below is a non-limiting and non-exhaustive list of excipients that are commonly used in the pharmaceutical arts. These excipients are commonly used in various types of formulations, including those formulated for intravenous, oral, intramuscular, or parenteral administration. Given the reactivity of chlorite, it is likely that some of the excipients listed below are inappropriate for a given pharmaceutical formulation. Whether or not a particular excipient is inappropriate for a given pharmaceutical formulation may depend upon the amount of the excipient being added to the pharmaceutical formulation. Before adding one or more of any excipient, including but not limited to the excipients described herein, to a pharmaceutical formulation of chlorite, it is important to consider the reactivity of the excipient with chlorite. Some organic molecules that are commonly used as excipients react with chlorite in such a way that the excipient is changed, including but not limited to a change that results in increased toxicity of the pharmaceutical formulation prior to exposure of the excipient to chlorite. In some variations, the pharmaceutical formulations described herein comprise one or more pharmaceutically acceptable excipients that do not react with chlorite. In another variation, the pharmaceutical formulations described herein comprise one or more pharmaceutically acceptable excipients that do not diminish the therapeutic effect of the pharmaceutical formulation relative to prior to exposure to the excipient.

In another variation, the chlorite formulations described herein comprise one or more pharmaceutically acceptable excipients that do not generate one or more of the deleterious non-chlorite elements of other commercially available chlorite formulations. In some variations, the chlorite formulations described herein comprise an excipient, and are substantially free of one or more of the deleterious non-chlorite elements of other commercially available chlorite formulations. In some variations, the chlorite formulations described herein comprise an excipient, and are substantially free of one or more of the degradation products or impurities of other commercially available chlorite formulations as described herein.

In some variations, the chlorite formulation comprises a stabilizer. Stabilizers include but are not limited to agents that will do any of (1) improve the compatibility of excipients with a container, including a glass bottle or an encapsulating materials such as gelatin, (2) improve the stability of chlorite (e.g. prevent degradation), or (3) improve formulation stability.

Stabilizers may be selected from, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. Amide analogues of stabilizers can also be used. The chosen stabilizer may change the hydrophobicity of the formulation (e.g., oleic acid, waxes), or improve the mixing of various components in the formulation (e.g., ethanol), control the moisture level in the formula (e.g., PVP or polyvinyl pyrrolidone), control the mobility of the phase (substances with melting points higher than room temperature such as long chain fatty acids, alcohols, esters, ethers, amides etc. or mixtures thereof waxes), and/or improve the compatibility of the formula with encapsulating materials (e.g., oleic acid or wax). Some of these stabilizers may be used as solvents/co-solvents (e.g., ethanol). Stabilizers may be present in sufficient amount to inhibit chlorite's degradation.

The formulations described herein may contain one or more of a gelling agent or a release modifying agent.

The formulations described herein may contain one or more adjuvants appropriate for the indicated route of administration. Again, prior to the addition of any excipient to the formulations described herein, the reactivity of chlorite should be considered with respect to whether the resulting pharmaceutical formulation will be appropriate for administration via the desired route of administration. Adjuvants with which the therapeutic agent may be admixed with include but are not limited to lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. When a solubilized formulation is required the therapeutic agent may be in a solvent including but not limited to polyethylene glycol of various molecular weights, propylene glycol of various molecular weights, carboxymethyl cellulose colloidal solutions, methanol, ethanol, DMSO, corn oil, peanut oil, cottonseed oil, sesame oil, tragacanth gum, and/or various buffers. Other adjuvants and modes of administration are well known in the pharmaceutical art and may be used in the practice of the methods and formulations described herein. The carrier or diluent may include time delay material, such as glyceryl monostearate or glyceryl distearate alone or with a wax, or other materials well known in the art. The formulations for use as described herein may also include gel formulations, erodible and non-erodible polymers, microspheres, and liposomes.

Additives and diluents normally utilized in the pharmaceutical arts can optionally be added to the pharmaceutical composition and the liquid formulation. These include thickening, granulating, dispersing, flavoring, sweetening, coloring, and stabilizing agents, including pH stabilizers, other excipients, anti-oxidants (e.g., tocopherol, BHA, BHT, TBHQ, tocopherol acetate, ascorbyl palmitate, ascorbic acid propyl gallate, and the like), preservatives (e.g., parabens), and the like. Exemplary preservatives include, but are not limited to, benzylalcohol, ethylalcohol, benzalkonium chloride, phenol, chlorobutanol, and the like. Some antioxidants provide oxygen or peroxide inhibiting agents and may be used in the formulations described herein, including but not limited to, butylated hydroxytoluene, butylhydroxyanisole, propyl gallate, ascorbic acid palmitate, α-tocopherol, and the like. Thickening agents, such as lecithin, hydroxypropylcellulose, aluminum stearate, and the like, may be used if desired, for example to improve one or more qualities of the formulation, such as the texture.

In some variations, the chlorite formulations described herein are sterile. Sterilization can be by any method that is compatible with chlorite. In some variations, sterilization is via a method that does not generate a substantial amount of a degradation product of chlorite. In some variations, sterilization is via a method that does not cause a structural change in chlorite. In some variations, the formulations described herein are sterile pharmaceutical formulations for parenteral or intravenous administration. In some variations, the chlorite formulations described herein are sterile filtered, for example, through a sterile 0.22 micron filter.

In some variations, the formulations or pharmaceutical formulations are sterile-filterable. In some variations, the chlorite formulations described herein are formulated for administration by one or more of the routes of administration described herein. A formulation that is "formulated for administration" by a specified route of administration, as used herein, is a formulation that does not include pharmaceutical excipients that are considered inappropriate for the route of administration by those of skill in the relevant art. As one example, a formulation that is suitable for intravenous administration would not include a toothpaste excipient or carrier intended for topical administration, where the excipient or carrier is considered inappropriate for the specified route of administration by those of skill in the relevant art.

Methods of Purifying Chlorite

Described herein are methods of purifying chlorite. It is intended that the methods described herein can be used to produce the formulations or pharmaceutical formulations described herein. However, the formulations and pharmaceutical formulations described herein may also be produced by other methods, and the formulations and pharmaceutical formulations described herein are not limited to those produced by the methods described herein.

In some variations, the purification is by subjecting a mixture comprising chlorite to conditions in which chlorite is in solution but one or more impurities are insoluble. The chlorite is separated from the insoluble impurities. In some variations, the chlorite is further purified by crystallization of the chlorite from the mixture, and separation of the chlorite from the remaining mixture. In some variations, the chlorite is purified from a mixture comprising sodium chlorite.

Generally, the chlorite ions may be from any source containing chlorite. For example, chlorite may be a chlorite salt, for example alkali metal salts, sodium chlorite, potassium chlorite, and the like, or a mixture of chlorite salts. Alternatively, the source of chlorite may be from a formulation comprising chlorite. In some variations, chlorite is purified from a formulation comprising TCDO or WF10. In another variation, chlorite is from a solution comprising sodium chlorite.

In some variations, impure chlorite, including but not limited to impure sodium chlorite, is dissolved in a solvent or a solvent system. In some variations, any solvent in which chlorite dissolves is used. In another variation, any solvent in which chlorite dissolves and with which chlorite does not react is used. In some variations, the solvent is distilled water. In some variations, the solvent is a non-organic solvent.

In some variations impure sodium chlorite is between about 0.1% to about 99% per weight of the starting material. As non-limiting examples of the purity of the chlorite starting material, the chlorite is between about any of 0.1% and about 5%; between about 1% and about 5%; between about 4% and about 10%; between about 1% and about 15%; between about 15% and about 25%; between about 5% and about 25%; between about 25% and about 50%; between about 50% and about 75%; between about 75% and about 85%; between about 85% to about 95%; between about 60% and about 90%; between about 95% and about 99% per weight of the starting material; at least about 50, at least about 60, at least about 70, at least about 80, at least about 90, or at least about 95% pure. If the impure chlorite is in a solvent, the percent purity is relative to the non-solvent components. In some variations the chlorite is between about 75% and about 85% pure. In some variations the chlorite is between about 85% and about 95% pure. In some variations the chlorite is at least about 85% pure.

In some variations, small amounts of hydrogen peroxide are added to the dissolved chlorite. While not wishing to be bound by theory, the addition of small amounts of hydrogen peroxide may reduce sodium chlorate to sodium chlorite. If desired, unreacted hydrogen peroxide may be subsequently removed. In some variations, hydrogen peroxide is added after the initial dissolution of chlorite step and subsequently removed by filtration, for example, by centrifugal filtration.

In some variations, an impure solution of chlorite is subjected to conditions wherein the chlorite remains soluble, but one or more of the impurities is no longer soluble. One such method is described in Russian Patent No. SU327132, which is hereby incorporated by reference in its entirety. In some variations, the impure solution is concentrated at an elevated temperature until one or more impurities precipitate. It is envisioned that the precipitated impurities can include but are not limited to chlorate, chloride, and sulfate. In some variations the impure solution is concentrated at a temperature that is any of between about 60 to about 100° C.; between about 65 to about 75° C.; between about 60 to about 80° C.; between about 60 to about 100° C.; between about 70 to about 90° C.; at about 60° C.; at about 65° C.; at about 70° C.; at about 75° C.; or at about 80° C. In some variations, the impure solution is concentrated at a temperature that is between about 65 to about 75° C.

In certain variations, the impure solution is concentrated using the methods described herein and under reduced pressure. A skilled artisan is familiar with a range of suitable techniques for providing reduced pressure including but not limited to the application of a vacuum during concentration.

The degree to which the chlorite solution is concentrated may be varied. In some variations, the solid to liquid phase volume ratio in the suspension is no greater than about 1 part to about 12 parts. By way of one non-limiting example, at least 50% water removal from a starting solution of chlorite has been demonstrated to result in the elimination of a significant amount of impurities, for example, chloride and/or chlorate, while maintaining chlorite in solution. One or more impurities are thereafter separated from the chlorite. In some variations the impurities are removed while the mixture is still subject to conditions wherein the chlorite remains soluble, but one or more of the impurities are no longer soluble. One method of removing the impurities is by filtration. If filtration is used, the temperature upon filtration may be, for example, at an elevated temperature that is similar to the temperature at which the concentration was performed. In some variations filtration is used, and the filtration occurs shortly after concentration. The concentrated chlorite solution includes greater than 80% pure chlorite by weight. The purity of chlorite in the concentrated solution can be greater than 85% pure or greater than 90% pure by weight.

The resulting chlorite solution may optionally be again subjected to conditions wherein the chlorite remains soluble, but one or more of the impurities is no longer soluble. The conditions may be optimized to reduce the same or a different impurity as was reduced in the first purification.

In some variations, the chlorite is subjected to conditions wherein the chlorite is not soluble, but the impurities are soluble. In some variations, chlorite is purified by inducing chlorite to crystallize from a solution. In some variations, the chlorite is induced to crystallize from a concentrated filtrate prepared by the methods described herein. As one non-limiting example, chlorite may be induced to crystallize by cooling the chlorite solution. In some variations, chlorite is induced to crystallize by exposure of a chlorite solution to a temperature that is any of no greater than about 10° C., no greater than about 0° C., no greater than about −10° C.; no greater than about −20° C.; no greater than about −30° C.; no greater than about −40° C.; between about −15° C. and about −35° C., between about −20° C. and about −30° C.; about 10° C.; about 0° C.; about −10° C.; about −15° C.; about −20° C.; about −25° C.; about −30° C.; about −35° C.; or about −40° C. In some variations, the chlorite is induced to crystallize by exposure of a chlorite solution to a temperature no greater than about −20° C. In some variations, the chlorite is induced to crystallize by exposure of a chlorite solution to a temperature between about −20° C. and about −30° C.

In general, the chlorite may be cooled at different rates, such as a stepwise placement into increasingly cool environments, or the chlorite formulation may be placed in a single cooling environment. The chlorite formulation may be cooled over a period of, for example, 12 to 24 hours. Longer or shorter periods may also be utilized. In some variations, the chlorite formulation is cooled over a period of between about 12 and about 14, about 14 and about 16, about 16 and about 18, about 18 and about 20, about 20 and about 22, or about 22 to about 24 hours.

In some variations, chlorite is harvested from a mixture comprising chlorite solids. The solids may be harvested by various methods known by those of skill in the art, including but not limited to by filtration. In some variations, chlorite solids are harvested from a mixture comprising chlorite that has been cooled to crystallize the chlorite solids.

In some variations, a mixture comprising chlorite solids is filtered as a frozen mixture comprising chlorite melts. When filtration is specified, those of skill in the art can determine an appropriate method of filtration. In some variations, suction filtration is used to separate chlorite solids from a mixture. The chlorite solids can be in the form of a slush. In another variation, centrifugal filtration is used to separate chlorite solids from a mixture. During centrifugal centrifugation, water remaining in the mixture containing chlorite solids melts and can be eliminated while the chlorite solids remain associated with a filter. In some variations, centrifugal filtration is performed using a 50 micron filter at 1200 rpm. In some variations the filter is about 50 to about 250 microns. In some variations, the rpm are about 1000 to about 3600. In another variation, the force of gravity is used to separate the solids from the rest of the mixture. The resulting chlorite solids can be in a hydrated form.

The chlorite may optionally be recrystallized by the above or a different method. In some variations the chlorite is recrystallized to give chlorite of increased purity relative to the first recrystallization.

Described herein are mixtures comprising chlorite, wherein the chlorite is any of greater than about 70%, greater than about 80%, greater than about 85%, greater than about 90%, greater than about 95%, greater than about 99%; between about 70-80%; between about 80-90%; between about 90-99%; about 70%; about 75%; about 80%; about 85%; about 90%; about 95%; or about 99% pure. If a solvent is present, including but not limited to water, the percentage purity is relative to the non-solvent components. Described herein are mixtures comprising chlorite, wherein the chlorite is between about 70-80% pure. Described herein are mixtures comprising chlorite, wherein the chlorite is between about 80-90% pure.

Purified chlorite may be dissolved in an aqueous solvent to give a chlorite solution of the desired concentration or molarity. As one example, the purified chlorite may be dissolved in distilled water or a saline solution, or any solvent, mixture of solvents, or solvent system that is capable of dissolving chlorite, or a solvent that is pharmaceutically acceptable for administration in a subject. Such a solvent is readily identified by those of skill in the art. See for example, Remington: The Science and Practice of Pharmacy, Twentieth Edition, Lippincott Williams & Wilkins; 20th edition (Dec. 15, 2000), which is incorporated herein by reference in its entirety. In some variations, the solvent is water. The resulting chlorite solution can include greater than 90% pure chlorite ions by weight. In some variations, the purity of chlorite in the solution can be greater than 95% pure chlorite ions or greater than 99% pure chlorite ions by weight. In one variation, wherein the purified chlorite is dissolved in water to an approximately 1M concentration, the solution can include a pH, for example, of about pH 8.5 to about pH 10.

Alternatively, the chlorite may be suspended in a suspending medium, including but not limited to any suspending medium that is capable of suspending chlorite, or a suspending medium that is pharmaceutically acceptable for administration in a subject. Such a suspending medium is readily identified by those of skill in the art. See, for example, Remington, cited above.

Briefly, one method of preparing a formulation comprising chlorite as disclosed herein can be achieve through the steps of: (a) concentrating a chlorite solution at a temperature between 60° C. to about 100° C., whereby impurities precipitate from the solution, (b) removing the impurities from the concentrated solution by filtration, (c) inducing crystallization of chlorite from the concentrated solution, (d) harvesting the resulting chlorite solids by filtration, and (e) dissolving the chlorite solids in an aqueous solvent. It is envisioned that in some variations the resulting aqueous formulation of chlorite comprises a purity of at least 80% chlorite, at least 85% chlorite, at least 90% chlorite, at least 95% chlorite or at least 99% chlorite.

The chlorite may also be emulsified in an emulsification system, including but not limited to any emulsification system that is capable of emulsifying chlorite, or an emulsification system that is pharmaceutically acceptable. Such an emulsification system is readily identified by those of skill in the art. See, for example, Remington, cited above.

Good Manufacturing Practice (GMP) Formulations and Methods

In general in another aspect, the invention provides chlorite formulations prepared under a standard relating to manufacture and quality control of pharmaceutical goods, called GMP (Good Manufacturing Practice), which has been enacted in many countries. GMP specifies, because of the importance of pharmaceutical goods which can decide one's life, that it is required to make quality control such as chemical analysis, to maintain optimum equipments and environments for manufacturing pharmaceutical goods, and to take care of all manufacturing practices including manufacture, packaging, display, and storage of pharmaceutical products and materials. GMP further refers to the Good Manufacturing Practice Regulations promulgated by the US Food and Drug Administration under the authority of the Federal Food, Drug, and Cosmetic Act. GMP is also sometimes referred to as "cGMP". The "c" stands for "current," reminding manufacturers that they must employ technologies and systems which are up-to-date in order to comply with the regulation. Systems and equipment used to prevent contamination, mix-ups, and errors, which may have been "top-of-the-line" 20 years ago, may be less than adequate by today's standards.

Accordingly, GMP is well known to those of skill in the art in relation to the manufacture of pharmaceutical goods. It is envisioned that the compositions and methods described herein can be manufactured and performed under GMP or cGMP.

Methods of Adjusting the pH of Formulations Sensitive to pH

Described herein are methods of adjusting the pH of formulations and pharmaceutical formulations comprising chlorite. It is intended that the methods described herein can be used to produce the formulations or pharmaceutical formulations described herein. However, the formulations and pharmaceutical formulations described herein may also be produced by other methods, and the formulations and pharmaceutical formulations described herein are not limited to those produced by the methods described herein.

Some compounds or formulations are sensitive to high local acidity or alkalinity. Yet it may be desired to adjust the pH of such compounds or formulations. Described herein are methods of adjusting the pH of formulations sensitive to high local acidity or alkalinity. Preferred pH adjusting agent(s) or pH adjusting compound(s) are weak acids or weak bases having a pKa of about 4 to about 9, a pKa of about 5 to about 9, or a pKa of about 5 to about 8, or a pKa of about 6 to about 7.5. Examples include, but are not limited to a phosphate buffer having a pKa of about 4 to about 9 as well known in the field, for example, monobasic phosphates, or monosodium phosphate, and lower alkanoic acids, for example, acetic acid or propionic acid. In some variations, the pH of a formulation sensitive to acidity is lowered to between about 7 and about 11.5 using a pH adjusting compound that does not expose the formulation to acidity, including but not limited to a high local acidity in the area around the pH adjusting compound. In some variations, the pH of a formulation sensitive to acidity is lowered to between about 7 and about 10 using a pH adjusting compound that does not expose the formulation to acidity, including but not limited to a high local acidity in the area around the pH adjusting compound. In some variations, the pH of a formulation sensitive to acidity is lowered to between about 7 and about 9.5 using a pH adjusting compound that does not expose the formulation to acidity, including but not limited to a high local acidity in the area around the pH adjusting compound. In some variations, the pH of a formulation sensitive to acidity is lowered to between about 7 and about 9.0 using a pH adjusting compound that does not expose the formulation to acidity, including but not limited to a high local acidity in the area around the pH adjusting compound. In some variations, the pH of a formulation sensitive to acidity is lowered to between about 7 and about 8.5 using a pH adjusting compound that does not expose the formulation to acidity, including but not limited to a high local acidity in the area around the pH adjusting compound. In some variations, the pH of a formulation sensitive to acidity is lowered to between about 7.1 and about 7.7 using a pH adjusting compound that does not expose the formulation to acidity, including but not limited to a high local acidity in the area around the pH adjusting compound.

"High local acidity," as used herein, refers to the pKa of one or more molecules local to a chlorite molecule, as opposed to the overall acidity of a solution as would be measured, for example, using a pH meter. To determine whether a pH-adjusting agent will subject chlorite to high local acidity, the pKa of the pH adjusting agent can be identified using, for example, the CRC Handbook of Chemistry and Physics (86th Edition, David R. Lide ed., CRC Press, 2005).

Lowering the pH of chlorite formulations has been challenging because many pH adjusting agents expose compounds or formulations to high acidity in the local area of the molecules of the pH-adjusting compound. In the presence of high local acidity, some amount of non-chlorite compounds are generated, for example, chlorate and/or chlorine dioxide. See, for example, Ullmann's Encyclopedia of Industrial Chemistry, Vol. A6, Ed. Wolfgang Gerhartz, 5th Ed. (1986), which is incorporated herein by reference in its entirety. Such degradation products may not be desired in formulations for parenteral or systemic administration to physiological systems, for example, because they are not inactive in physiological systems. Some such degradation products result in toxicity, including but not limited to the toxicities, including but not limited to non-specific toxicity, described herein.

Unless the context makes clear, the pH of any of the formulations or pharmaceutical formulations described herein may be adjusted using the methods described herein.

In some variations, the activity of a therapeutic agent, including but not limited to chlorite, is diminished by exposure to high local acidity. "Diminished activity," as used herein, refers to an activity of a therapeutic agent that is qualitatively or quantitatively inferior to that of the therapeutic agent prior to the exposure to high local acidity. As one example, a changed activity that is qualitatively or quantitatively inferior to that of the therapeutic agent prior to the exposure to high local acidity would be a lesser efficacy of wound healing, or a lesser efficacy in treating one or more of the diseases or conditions described herein. In some variations, the changed activity is any of at least about 3%, at least about 5%, at least about 10%, at least about 15%, at least about 20%, or at least about 25% lower than the activity of the therapeutic agent prior to the exposure to high local acidity. In some variations, the changed activity is at least about 5% lower than the activity of the therapeutic agent prior to the exposure to high local acidity.

In some variations, the pH of a chlorite formulation is adjusted to any one or more of the pH levels described in the formulations section or elsewhere herein. In some variations the pH of a chlorite formulation described between about 7 and about 11.5. In some variations, the method comprises lowering the pH of a formulation comprising chlorite to any of between about between about 7 and about 11; between about 7 and about 10.5; between about 7 and about 10; between about 7 and about 9.5; between about 7 and about 9; between about 7 and about 8.5; between about 7 and about 8.0; between about 7 and about 7.5; between about 7.5 and about 8; between about 7.5 and about 8.5; between about 7 and about 8; between about 7.1 and about 7.7; between about 7.2 and about 7.6; between about 7.3 and about 7.5; between about 8 and about 9; between about 8 and about 8.5; between about 8.5 and about 9; about 7.0; about 7.1; about 7.2; about 7.3; about 7.4; about 7.5; about 7.6; about 7.7; about 7.8; about 7.9; about 8.0; about 8.1; about 8.2; about 8.3; about 8.4; about 8.5; about 8.6; about 8.7; about 8.8; or about 8.9 using a pH adjusting agent that does not expose the chlorite to a high local acidity. In some variations, the method comprises lowering the pH of a formulation comprising chlorite to between about 7 and about 8.5. In some variations, the method comprises lowering the pH of a formulation comprising chlorite to between about 7 and about 8.0. In some variations, the method comprises lowering the pH of a formulation comprising chlorite to between about 7.1 and about 7.7. In some variations, the method comprises lowering the pH of a formulation comprising chlorite to about 7.4.

In one nonlimiting example, the pH of a mixture comprising chlorite is adjusted using a pH adjusting agent that does not subject the chlorite to a local pH of below 7 when exposed to the mixture comprising chlorite. In some variations, the pH adjusting agent is monosodium phosphate. In further variations, monosodium phosphate is used as a solid or in solution. In some variations, the pH adjusting agent is acetic acid.

In some variations, the pH of chlorite is adjusted by adding chlorite or an aqueous mixture comprising chlorite to a solution containing buffer. In some variations, the pH of chlorite is adjusted by adding chlorite or an aqueous mixture comprising chlorite to a solution of a phosphate buffer.

In some variations, one or more pH-adjusting agents are used to adjust the pH of a chlorite solution or mixture, and the resulting solution or mixture is analyzed for the presence of degradation products of chlorite, including but not limited to degradation products generated by high local acidity. In some variations, pH-adjusting agents such as acetic acid, or monosodium phosphate are used to adjust the pH of a chlorite solution or mixture, and the resulting solution or mixture is analyzed for the presence of chlorate or chlorine dioxide.

In some variations, the resulting solution or mixture is analyzed for degradation products using well known analytical methods such as HPLC, mass spectrometry, etc. In another variation, the resulting solution or mixture is analyzed for degradation products using a toxicity assay, including well-known toxicity assays. In some variations the resulting solution or mixture is analyzed for impurities using a non-specific toxicity assay such as the one described in Example 4 below.

In some variations, the pH of a chlorite formulation is adjusted after a chlorite purification step.

In some variations, the pH of a chlorite formulation is adjusted to between about 7 and about 11.5 without the generation of chlorite degradation products that are a result of high local acidity. In some variations, the pH of a chlorite formulation is adjusted to between about 7 and about 8.0 without the generation of chlorite degradation products that are a result of high local acidity. In some variations, the pH of the chlorite formulation is adjusted to any of between about 7 and about 11; between about 7 and about 10.5; between about 7 and about 10; between about 7 and about 9.5; between about 7 and about 9; between about 7 and about 8.5; between about 7 and about 8; between about 7 and about 7.5; between about 7.5 and about 8; between about 7.5 and about 8.5; between about 7 and about 8; between about 8 and about 9; between about 8 and about 8.5; or between about 8.5 and about 9 without the generation of chlorite degradation products that are a result of high local acidity.

Methods of Treatment

As noted previously, numerous conditions can be treated using the chlorite formulations described herein. Unless the context indicates otherwise, all of the formulations and pharmaceutical formulations described herein may be used in the methods of treatment described herein. As used herein and as well understood in the art, examples of treatment include obtaining beneficial or desired results, including clinical results. As described herein, nonlimiting examples of beneficial or desired clinical results include one or more of, but are not limited to, alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease, state, and remission (whether partial or total), whether detectable or undetectable. In some variations, the chlorite formulations described herein are used to achieve one or more of treating, preventing, delaying the onset of, or causing the regression of the diseases or conditions described herein.

In general, a therapeutically effective amount of a formulation is administered to a subject. An "effective amount," which is also referred to herein as a "therapeutically effective amount," of a therapeutic agent for administration as described herein is that amount of the therapeutic agent that provides the therapeutic effect sought when administered to the subject. A therapeutically effective amount may be achieved in a single administration or after multiple administrations. The achieving of different therapeutic effects may require different effective amounts of therapeutic agent. For example, the therapeutically effective amount of a therapeutic agent used for preventing a disease or condition may be different from the therapeutically effective amount used for treating, inhibiting, delaying the onset of, or causing the regression of the disease or condition. In addition, the therapeutically effective amount may depend on the age, weight, the bioavailability of the compound, the severity of the disease or condition, and other health conditions of the subject as is well know to those versed in the disease or condition being addressed. Thus, the therapeutically effective amount may not be the same in every subject to which the therapeutic agent is administered.

To determine whether a level of therapeutic agent is a "therapeutically effective amount" to treat the diseases or conditions described herein, the chlorite formulations may be administered in appropriate animal models for the diseases or conditions of interest, and the effects may be observed to determine whether the treatment was effective in the animal model. The appropriate level for a different subject, including but not limited to a human subject, may be estimated therefrom using methods known by those of skill in the art.

Effective dosages may be estimated initially from in vitro assays. For example, an initial dosage for use in animals may be formulated to achieve a circulating blood or serum concentration of active compound that is at or above an IC50 of the particular compound as measured in an in vitro assay. Calculating dosages to achieve such circulating blood or serum concentrations, taking into account the bioavailability of the particular active agent, is well within the capabilities of skilled artisans. For guidance, the reader is referred to Fingl & Woodbury, "General Principles," *In: Goodman and Gilman's The Pharmaceutical Basis of Therapeutics*, Chapter 1, pp. 1-46, latest edition, Pergamagon Press, which is hereby incorporated by reference in its entirety, and the references cited therein.

The chlorite formulations described herein can be administered alone, or administered in combination with or adjunctive to other common therapies for treating the diseases or conditions described herein. Administration of the chlorite formulation may be prior to, subsequent to, or concurrent with one or more other treatments, including but not limited to treatments using other active agents or non-pharmaceutical therapies such as radiotherapy. In some variations the chlorite or other therapeutic agents are used in accordance with their standard or common dosages, as specified in the prescribing information accompanying other commercially available chlorite formulations (see also, the prescribing information in the 2005 Edition of The Physician's Desk Reference), the disclosures of which are incorporated herein by reference).

As mentioned above, chlorite has been used to treat various diseases or conditions using previously described chlorite formulations. Unless the context makes otherwise clear, all of the chlorite formulations and pharmaceutical formulations described herein may be used to treat diseases or conditions treated with previously described chlorite formulations. For example, chlorite has been used to treat infections and to cause regeneration of bone marrow. See, for example, U.S. Pat. Nos. 4,725,437 and 4,851,222, each of which is incorporated herein by reference in its entirety. Chlorite has also been used to treat HIV, recurrent prostate cancer, cystitis, and chronic active hepatitis C disease. See, for example, McGrath et al., Development of WF10, a novel macrophage-regulating agent, *Curr Opin Investig Drugs*, 3(3):365-73 (March 2002); U.S. Pat. No. 6,086,922, each of which is incorporated herein by reference in its entirety.

Other non-limiting examples of diseases or conditions that may be treated with the formulations and pharmaceutical formulations described herein include those described in US Patent Pub. No. 2005/0181068 (Ser. No. 11/042,816) to McGrath ("McGrath"), which is incorporated herein by reference in its entirety. McGrath describes methods of treating neurodegenerative diseases by administering chlorite in an effective amount to treat such diseases. In some variations, the neurodegenerative disease or disorder is a macrophage-associated neurodegenerative disease or disorder. In some variations, the neurodegenerative disease or disorder treated using the formulations and pharmaceutical formulations described herein is amyotrophic lateral sclerosis (ALS), Alzheimer's disease (AD), multiple sclerosis (MS), pathogen-associated neural diseases or symptoms, such as viral infection, including but not limited to HIV-associated dementia (HAD), or HCV infection. In some variations, ALS is treated using the formulations and pharmaceutical formulations described herein. In some variations, AD is treated using the formulations and pharmaceutical formulations described herein.

It is envisioned that neoplasia may be treated with the formulations and pharmaceutical formulations described herein. Neoplasia is generally defined as abnormal, disorganized growth in a tissue or organ. Such a growth can be in the form of a mass, often called a neoplasm, tumor or cancer. Neoplasms can be benign or malignant lesions. Malignant lesions are often called cancer. The National Institute of Health lists thirteen cancers as the most frequently diagnosed in the United States, each having an estimated annual incidence for 2006 at 30,000 cases or more. These most frequently diagnosed cancers include: bladder cancer, melanoma, breast cancer, non-Hodgkin's lymphoma, colon and rectal cancer, pancreatic cancer, endometrial cancer, prostate cancer, kidney (renal cell) cancer, skin cancer (non-melanoma), leukemia, thyroid cancer and lung cancer. Source: http://www.cancer.gov/cancertopics/commoncancers. Last accessed Sep. 12, 2006.

An extensive listing of cancer types includes but is not limited to acute lymphoblastic leukemia (adult), acute lymphoblastic leukemia (childhood), acute myeloid leukemia (adult), acute myeloid leukemia (childhood), adrenocortical carcinoma, adrenocortical carcinoma (childhood), AIDS-related cancers, AIDS-related lymphoma, anal cancer, astrocytoma (childhood cerebellar), astrocytoma (childhood cerebral), basal cell carcinoma, bile duct cancer (extrahepatic), bladder cancer, bladder cancer (childhood), bone cancer (osteosarcoma/malignant fibrous histiocytoma), brain stem glioma (childhood), brain tumor (adult), brain tumor—brain stem glioma (childhood), brain tumor—cerebellar astrocytoma (childhood), brain tumor—cerebral astrocytoma/malignant glioma (childhood), brain tumor—ependymoma (childhood), brain tumor—medulloblastoma (childhood), brain tumor—supratentorial primitive neuroectodermal tumors (childhood), brain tumor—visual pathway and hypothalamic glioma (childhood), breast cancer (female, male, childhood), bronchial adenomas/carcinoids (childhood), Burkitt's lymphoma, carcinoid tumor (childhood), carcinoid tumor (gastrointestinal), carcinoma of unknown primary site (adult and childhood), central nervous system lymphoma (primary), cerebellar astrocytoma (childhood), cerebral astrocytoma/malignant glioma (childhood), cervical cancer, chronic lymphocytic leukemia, chronic myelogenous leukemia, chronic myeloproliferative disorders, colon cancer, colorectal cancer (childhood), cutaneous t-cell lymphoma, endometrial cancer, ependymoma (childhood), esophageal cancer, esophageal cancer (childhood), Ewing's family of tumors, extracranial germ cell tumor (childhood), extragonadal germ cell tumor, extrahepatic bile duct cancer, eye cancer (intraocular melanoma and retinoblastoma), gallbladder cancer, gastric (stomach) cancer, gastric (stomach) cancer (childhood), gastrointestinal carcinoid tumor, gastrointestinal stromal tumor (gist), germ cell tumor (extracranial (childhood), extragonadal, ovarian), gestational trophoblastic tumor, glioma (adult), glioma (childhood: brain stem, cerebral astrocytoma, visual pathway and hypothalamic), hairy cell leukemia, head and neck cancer, hepatocellular (liver) cancer (adult primary and childhood primary), Hodgkin's lymphoma (adult and childhood), Hodgkin's lymphoma during pregnancy, hypopharyngeal cancer, hypothalamic and visual pathway glioma (childhood), intraocular melanoma, islet cell carcinoma (endocrine pancreas), Kaposi's sarcoma, kidney (renal cell) cancer, kidney cancer (childhood), laryngeal cancer, laryngeal cancer (childhood), leukemia—acute lymphoblastic (adult and childhood), leukemia, acute myeloid (adult and childhood), leukemia—chronic lymphocytic, leukemia—chronic myelogenous, leukemia—hairy cell, lip and oral cavity cancer, liver cancer (adult primary and childhood primary), lung cancer—non-small cell, lung cancer—small cell, lymphoma—AIDS-related, lymphoma—Burkitt's, lymphoma—cutaneous t-cell, lymphoma—Hodgkin's (adult, childhood and during pregnancy), lymphoma—non-Hodgkin's (adult, childhood and during pregnancy), lymphoma—primary central nervous system, macroglobulinemia—Waldenström's, malignant fibrous histiocytoma of bone/osteosarcoma, medulloblastoma (childhood), melanoma, melanoma—intraocular (eye), Merkel cell carcinoma, mesothelioma (adult) malignant, mesothelioma (childhood), metastatic squamous neck cancer with occult primary, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia, chronic, myeloid leukemia (adult and childhood) acute, myeloma—multiple, myeloproliferative disorders—chronic, nasal cavity and paranasal sinus cancer, nasopharyngeal cancer, nasopharyngeal cancer (childhood), neuroblastoma, non-small cell lung cancer, oral cancer (childhood), oral cavity and lip cancer, oropharyngeal cancer, osteosarcoma/malignant fibrous histiocytoma of bone, ovarian cancer (childhood), ovarian epithelial cancer, ovarian germ cell tumor, ovarian low malignant potential tumor, pancreatic cancer, pancreatic cancer (childhood), pancreatic cancer—islet cell, paranasal sinus and nasal cavity cancer, parathyroid cancer, penile cancer, pheochromocytoma, pineoblastoma and supratentorial primitive neuroectodermal tumors (childhood), pituitary tumor, plasma cell neoplasm/multiple myeloma, pleuropulmonary blastoma, pregnancy and breast cancer, primary central nervous system lymphoma, prostate cancer, rectal cancer, renal cell (kidney) cancer, renal cell (kidney) cancer (childhood), renal pelvis and ureter—transitional cell cancer, retinoblastoma, rhabdomyosarcoma (childhood), salivary gland cancer, salivary gland cancer (childhood), sarcoma—Ewing's family of tumors, sarcoma—Kaposi's, sarcoma—soft tissue (adult and childhood), sarcoma—uterine, Sézary syndrome, skin cancer (non-melanoma), skin cancer (childhood), skin cancer (melanoma), skin carcinoma—Merkel cell, small cell lung cancer, small intestine cancer, soft tissue sarcoma (adult and childhood), squamous cell carcinoma, squamous neck cancer with occult primary—metastatic, stomach (gastric) cancer, stomach (gastric) cancer (childhood), supratentorial primitive neuroectodermal tumors (childhood), testicular cancer, thymoma (childhood), thymoma and thymic carcinoma, thyroid cancer, thyroid cancer (childhood), transitional cell cancer of the renal pelvis and ureter, trophoblastic tumor, gestational, ureter and renal pelvis—transitional cell cancer, urethral cancer, uterine cancer—endometrial, uterine sarcoma, vaginal cancer, visual pathway and hypothalamic glioma (childhood), vulvar cancer, Waldenstrom's macroglobulinemia, and Wilms' tumor. Source: http://www.cancer.gov/cancertopics/alphalist. Last accessed Sep. 12, 2006.

Routes of Administration

Unless the context indicates otherwise, all of the formulations and pharmaceutical formulations described herein may be administered by any of systemic, parenteral (e.g., intramuscular, intraperitoneal, intravenous, ICV, intracisternal injection or infusion, subcutaneous injection, or implant), by inhalation spray, nebulised or aerosolized using aerosol propellants, nasal, vaginal, rectal, sublingual, urethral (e.g., urethral suppository), by infusion, intraarterial, intrathecal, intrabronchial, subcutaneous, intradermal, intravenous, intracervical, intraabdominal, intracranial, intrapulmonary, intrathoracic, intratracheal, nasal routes, oral administration that delivers the therapeutic agent systemically, drug delivery device, or by a dermal patch that delivers the therapeutic agent systemically, transdermally or transbuccally. In some variations, the formulation is formulated for other than oral or transbuccal administration.

In some variations, the formulations described herein are not administered topically.

In some embodiments, the formulations, pharmaceutical formulations, and methods of administration and treatment described herein are suitable for use in any warm- or cold-blooded animal. In some embodiments, the formulations, pharmaceutical formulations, and methods of administration and treatment described herein are suitable for use in a mammal, including in the veterinary context, including domestic pets (such as cats, dogs, rabbits, birds, horses, etc.) and agricultural animals (such as bovine, ovine, fowl, etc.). In some variations, the formulations, pharmaceutical formulations, and methods of administration and treatment described herein are suitable for use in primates, including but not limited to humans.

Kits and Articles of Manufacture

Unless the context makes otherwise clear, all of the formulations and pharmaceutical formulations described herein may be used in the kits described herein. Provided herein are kits for administration of chlorite or pharmaceutical formulations comprising chlorite that may include a unit dosage amount of a chlorite formulation as described herein. In some variations, the kits comprise suitable packaging. In some variations, the kits comprise instructions for use of the chlorite formulations to treat various diseases or conditions. Accordingly, the kits may be used for any of the treatment methods described herein, and in some embodiments contain suitable instructions for practicing any of the treatment methods described herein. In some embodiments, the kits are used to treat any one or more of the diseases or conditions described herein. Kits may also comprise an aid to administration of the chlorite formulation, such as an inhaler, spray dispenser (e.g. nasal spray), syringe for injection or pressure pack for capsules, tablets, or suppositories.

The chlorite formulations described herein may be assembled in the form of kits. In some variations the kit provides the chlorite and reagents to prepare an aqueous chlorite formulation for administration. In some variations the formulation is an aqueous solution. In some variations the formulation is a sterile solution. In some variations, a kit provides a pharmaceutically acceptable diluent, either already mixed with the formulations or formulations described herein or provided in a separate container from the formulations or pharmaceutical formulations described herein. In some variations, the diluent is a saline solution. In some variations, the composition comprises a dry (such as lyophilized) composition that can be reconstituted or dissolved to form the formulations or pharmaceutical formulations described herein. When the formulation is in a dry form, the kit may comprise one or more of a pharmaceutically acceptable solvent, diluent, and a pH adjusting agent, either separately from or as part of the diluent. In some variations, a kit or article of manufacture comprises chlorite in dry form, a pharmaceutically acceptable solvent, and pH adjusting agent. In some variations the pH adjusting agent is incorporated into the solvent. In some variations, a kit or article of manufacture comprises chlorite in dry form, a pharmaceutically acceptable solvent, a pharmaceutically acceptable diluent, and pH adjusting agent. In some variations the pH adjusting agent is incorporated into the diluent. In some variations, the formulations or pharmaceutical formulations described herein are sterile, reconstituted formulations. In some variations, the formulations or pharmaceutical formulations described herein are sterile, reconstituted formulations in unit dosage form. In some variations, the formulations or pharmaceutical formulations described herein are sterile, reconstituted formulations in unit dosage form in suitable packaging.

The kit may contain a device for administration or for dispensing the compositions, including, but not limited to one or more syringes, pipettes, transdermal patches, or inhalants.

The kit may include other therapeutic compounds or formulations for use in conjunction with the formulations described herein. These compounds may be provided in a separate form, or mixed with the chlorite formulations or pharmaceutical formulations described herein.

In some variations the kit includes instructions for preparation and administration of the formulation. In some variations the kit includes instructions as to side effects of the formulation. In another variation the kit optionally includes any other relevant information. The instructions may be in any suitable format, including, but not limited to, printed matter, videotape, computer readable disk, or optical disc. The instructions may be located inside the housing or outside the housing, and may be printed on the interior or exterior of any surface forming the housing that renders the instructions legible.

Described herein are kits for treating an individual who suffers from or is susceptible to a disease or condition treatable by the chlorite formulations described herein, comprising a container comprising a unit dosage amount of a chlorite formulation as described herein, and instructions for use. The container may be any of those known in the art and appropriate for storage and delivery of oral, intravenous, systemic, parenteral, rectal, urethral, transdermal, or inhalation formulations.

Kits may also be provided that contain sufficient dosages of the chlorite or chlorite formulation to provide effective treatment for an individual for an extended period, including but not limited to any of about a week, about 2 weeks, about 3 weeks, about 4 weeks, about 6 weeks or about 8 weeks or more.

Figure 2:
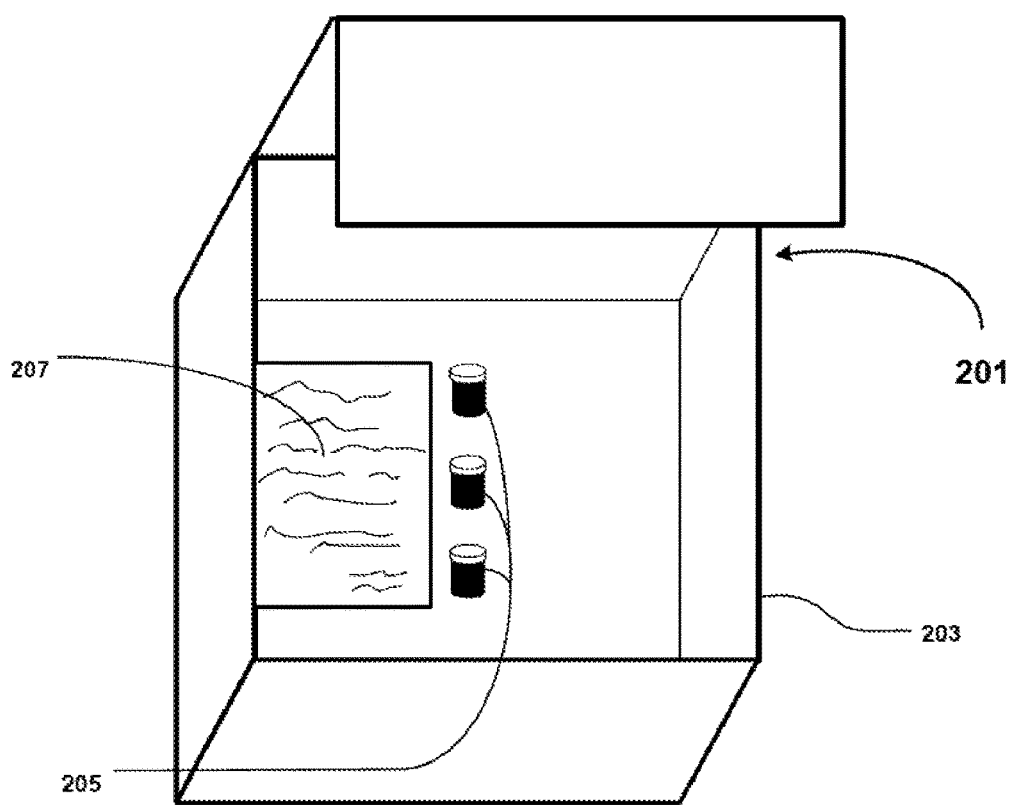
FIG. 2 is a block diagram showing a representative example of a kit.

As described herein and shown in FIG. 2, in certain embodiments a kit 201 can include a housing or container 203 for housing various components. As shown in FIG. 2 and described herein, the kit 201 can optionally include instructions 207 as well as reagents 205, for example the formulations described herein. Other embodiments of the kit 201 are envisioned wherein the components include various additional features described herein.

Also provided herein are articles of manufacture comprising the formulations or pharmaceutical formulations described herein, or unit dosage forms in suitable packaging, including but not limited to vials or vessels, including but not limited to sealed vials or vessels and sterile sealed vials or vessels. Non-limiting examples of suitable packaging for the formulations and pharmaceutical formulations described herein are known in the art, and include, for example, any of vials (such as sealed vials), vessels (such as sealed vessels), ampules, bottles, jars, flexible packaging (e.g., sealed Mylar or plastic bags), and the like. Such packaging may optionally limit the amount of light to which the formulation is exposed. These articles of manufacture may further be sterilized and/or sealed.

The invention is further illustrated by the following non-limiting examples.

EXAMPLES

Example 1

Purification of Chlorite

This procedure was performed in diminished light, e.g., with overhead lights off, and out of direct sunlight.

Sodium Chlorite (80 wt %, Sigma-Aldrich lot #09911CD) was dissolved in 1000 mL of distilled water. The flask was mounted to a rotary evaporator, and the bath temperature set to 70° C. Vacuum was applied, and increased until the water began to distill over in a controlled manner. The vacuum was applied until the mixture put down a load of solids, and 550 mL of water had distilled over. Using a coarse sintered glass funnel, the solids were removed by suction filtration of the hot solution. These solids were mostly sodium chloride.

The filtrate was stored at −25° C. for a period of time sufficient to precipitate the chlorite (approximately 24 hours). The entire mixture froze solid. The frozen mixture was broken up and centrifugally filtered while cold. Purified sodium chlorite was collected as the frozen solid melted. The centrifuge had a 12-inch stainless steel basket, 50 micron polypropylene bag, and was run at 2000 rpm. HPLC analysis using an ion-separating column and ion detector showed 99.04% purity. The material is presumed to be a mixture of hydrate and non-hydrate.

Example 2

Purification of Chlorite

The method described in Example 1 was performed, but using coarse sintered glass suction filtration rather than centrifugal filtration for the cold filtration. After the first filtration, chlorite purity after the first crystallization was 91.9%. The crystallization step was repeated a second time. After the second recrystallization/suction filtration, the chlorite was 99.5% pure.

Example 3

Adjustment of Chlorite Formulation pH

To prepare a chlorite formulation at a lower pH, sodium chlorite purified by the method of Example 2 was dissolved in distilled water and stirred using a magnetic stirrer. A calibrated pH probe was put in the solution. Small amounts of monosodium phosphate monohydrate were added, until the pH reached and stabilized at 7.62. In the event of the pH drifting lower than the target pH, the pH can be adjusted back with 0.1 N NaOH.

This solution was sampled, and assayed for sodium chlorite content by HPLC. Column: Novosep A-2 Alltech 250×4 mm; eluant: 3.6 mM sodium carbonate. Rate: 0.8 mL/min. Detected with a suppressed Alltech 650 conductivity detector. Quantitation was performed by standard iodimetry. See Inorganic Syntheses, section under Chlorine (IV) Oxide; Sodium Chlorite analysis, p. 156. The concentration was determined to be 1.36 M. To prepare a 4.25 wt % solution (0.47 M), 200 mL were diluted to 580 mL.

Example 4

Toxicity

Jurkat T cells (cell line) were used to test nonspecific toxicity of a chlorite formulation as described herein versus WF10. The formulation tested against WF10 was chlorite in water, with saline as a diluent. The formulation was adjusted to a pH of about 7.4 using the method described in Example 3, with sodium phosphate as buffer. The chlorite was at greater than about 95% purity. Triplicate cultures of Jurkat T cells were exposed to various concentrations of each chlorite formulation for 24 hours at 37° C. The number of live cells for each concentration treatment was normalized to untreated cultures and plotted. Cell viability was measured by trypan blue exclusion. Trypan Blue is a dye that is used to determine the viability of a cell. Living cells exclude the dye, whereas dead cells take up the dye. The blue stain is easily visible, and cells can be counted using a light microscope. The results are shown in FIG. 1. Based on the relative numbers of live cells, WF10 treatment resulted in nonspecific toxicity at concentrations of 50 μM and higher, whereas TJ001 did not result in nonspecific toxicity until concentrations of 200 μM and higher.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of administering chlorite, wherein the method comprises parenterally administering to a subject in need thereof a therapeutically effective amount of an aqueous formulation comprising an aqueous solvent, a pH adjusting agent comprising phosphate, and chlorite, wherein said chlorite is purified to greater than about 95% chlorite ions to non-chlorite ions.

2. The method of claim 1, wherein the weight ratio of chlorite:chlorate is greater than 100:1.5.

3. The method of claim 1, wherein the ratio of chlorite:chlorate is greater than 100:0.5.

4. The method of claim 1, wherein the aqueous formulation is substantially free of chlorate.

5. The method of claim 1, which the aqueous formulation substantially free of chlorine dioxide.

6. The method of claim 1, wherein the weight ratio of chlorite:sulfate is greater than 100:16.4.

7. The method of claim 1, wherein the weight ratio of chlorite:sulfate is greater than 100:1.6.

8. The method of claim 1, wherein the aqueous formulation is substantially free of sulfate.

9. The method of claim 1, wherein the weight ratio of chlorite:chloride is greater than 100:10.

10. The method of claim 1, wherein the pH of the aqueous formulation is between about 7.0 and about 11.5.

11. The method of claim 1, wherein the pH of the aqueous formulation is between about 7.0 and 9.

12. The method of claim 1, wherein the pH modifying agent is a phosphate buffer.

13. The method of claim 1, wherein the pH modifying agent is monosodium phosphate.

14. The method of claim 1, wherein the aqueous formulation is administered intravenously.

15. The method of claim 1, wherein the aqueous formulation is for the treatment of a neurodegenerative disorder.

16. The method of claim 15, wherein the neurodegenerative disorder is amyotrophic lateral sclerosis (ALS).

* * * * *